US010618962B2

(12) United States Patent
Sun et al.

(10) Patent No.: US 10,618,962 B2
(45) Date of Patent: Apr. 14, 2020

(54) ANTI-CTLA4 ANTIBODIES

(71) Applicant: CROWN BIOSCIENCE (TAICANG) INC., Taicang, Jiangsu (CN)

(72) Inventors: Ziyong Sun, Taicang (CN); Man Zhou, Taicang (CN); Wencui Ma, Taicang (CN); Hongli Ma, Taicang (CN); Wei Chen, Taicang (CN)

(73) Assignee: CROWN BIOSCIENCE (TAICANG) INC., Taicang, Jiangsu (CN)

( * ) Notice: Subject to any disclaimer, the term of this patent is extended or adjusted under 35 U.S.C. 154(b) by 0 days.

(21) Appl. No.: 16/338,698

(22) PCT Filed: Oct. 10, 2016

(86) PCT No.: PCT/CN2016/101681
§ 371 (c)(1),
(2) Date: Apr. 2, 2019

(87) PCT Pub. No.: WO2018/068182
PCT Pub. Date: Apr. 19, 2018

(65) Prior Publication Data
US 2019/0225690 A1 Jul. 25, 2019

(51) Int. Cl.
*C07K 16/28* (2006.01)
*A61P 35/00* (2006.01)
*A61K 39/395* (2006.01)
*A61P 37/04* (2006.01)
*A61K 39/00* (2006.01)

(52) U.S. Cl.
CPC ........ *C07K 16/2818* (2013.01); *A61K 39/395* (2013.01); *A61P 35/00* (2018.01); *A61P 37/04* (2018.01); *C07K 16/28* (2013.01); *A61K 2039/505* (2013.01); *C07K 2317/24* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 1,762,703 | A | | 6/1930 | Smith |
| 2,944,295 | A | | 7/1960 | Sloan |
| 8,101,183 | B2 | * | 1/2012 | Siadak ................. C07K 16/244 424/145.1 |
| 2013/0184135 | A1 | | 7/2013 | Duer |

FOREIGN PATENT DOCUMENTS

| AT | 512 357 A1 | 7/2013 |
| CN | 105296433 A | 2/2016 |
| DE | 2 44 724 A1 | 4/1987 |
| EP | 0 054 907 A2 | 6/1982 |
| WO | 2013/142796 A2 | 9/2013 |
| WO | 2015/010727 A1 | 1/2015 |

OTHER PUBLICATIONS

Mariuzza, R.A. etal. The Structural Basis of Antigen-Antibody Recognition1 Annu. Rev. Biophys. Biphys. Chem. 16:139-159, 1987.*
Rowshanravan et al. 'CTLA-4: a moving target in immunotherapy.' Blood. 131(1):58-67, 2018.*
Maccallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
Goel et al. Plasticity within the Antigen-Combining Site May Manifest as Molecular Mimicry in the Humoral Immune Response. 1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*
Poosarla et al. 'Computational De Novo Design of Antibodies Binding to a Peptide With High Affinity.' Biotech. Bioeng. 114(6): 1331-1342, 2017.*
Ham, R. G. et al., "Media and Growth Requirements", Methods in Enzymology (1979), vol. LVIII, pp. 44-93.
Barnes, D. et al., "Methods for growth of cultured cells in serum-free medium", Analytical Biochemistry (1980), vol. 102(2), pp. 255-270.
Carter, P. et al., "High level *Escherichia coli* expression and production of a bivalent humanized antibody fragment", Bio/Technology (1992), vol. 10(2), p. 163-167.
Lindmark, R. et al., "Binding of immunoglobulins to protein A and immunoglobulin levels in mammalian sera", Journal of Immunological Methods (1983), vol. 62(1), pp. 1-13.
Guss, B. et al., "Structure of the IgG-binding regions of streptococcal protein G", The EMBO journal (1986), vol. 5(7), pp. 1567-1575.
Kettleborough, C. A. et al., "Optimization of primers for cloning libraries of mouse immunoglobulin genes using the polymerase chain reaction", European Journal of Immunology (1993), vol. 23(1), pp. 206-211.
Strebe, N. et al., "Cloning of Variable Domains from Mouse Hybridoma by PCR", Antibody Engineering (2010). vol. 1, pp. 3-14.
Bretscher, P. et al., "A theory of self-nonself discrimination" , Science (1970), vol. 169(3950), pp. 1042-1049.
Bernard, A. et al., "The Two-Signal Model of T-Cell Activation After 30 Years", Transplantation (2002), vol. 73, No. 1, pp. S31-S35.

(Continued)

*Primary Examiner* — Nora M Rooney
(74) *Attorney, Agent, or Firm* — Jun He Law Offices P.C.; James J. Zhu

(57) ABSTRACT

The present disclosure provides antibodies and antigen binding fragments against CTLA4, which can block the binding of CTLA4 to its ligand. The antibodies of disclosure provide agents for treating diseases, such as cancer.

13 Claims, 7 Drawing Sheets

Specification includes a Sequence Listing.

(56) References Cited

OTHER PUBLICATIONS

Brunet, J-F. et al., "A new member of the immunoglobulin superfamily—CTLA-4", Nature (1987), vol. 328(6127), pp. 267-270.
Stamper, C. C. et al., "Crystal structure of the B7-1/CTLA-4 complex that inhibits human immune responses", Nature (2001), vol. 410(6828), pp. 608-611.
Rudd, C. E. et al., "CD28 and CTLA-4 coreceptor expression and signal transduction", Immunological Reviews (2009), pp. 12-26.
Peach, R. J. et al, "Complementarity determining region 1 (CDR1)- and CDR3-analogous regions in CTLA-4 and CD28 determine the binding to B7-1", Journal of Experimental Medicine (1994), vol. 180(6), pp. 2049-2058.
Calvo, C. R. et al., "Cytotoxic T Lymphocyte Antigen 4 (CTLA-4) Interferes with Extracellular Signal-regulated Kinase (ERK) and Jun NH2-terminal Kinase (JNK) Activation, but Does Not Affect Phosphorylation of T Cell Receptor ζ and ZAP70", The Journal of Experimental Medicine (1997), vol. 186(10), pp. 1645-1653.
Mellor, A. L. et al., "Specific subsets of murine dendritic cells acquire potent T cell regulatory functions following CTLA4-mediated induction of indoleamine 2,3 dioxygenase", International Immunology (2004), vol. 16(10), pp. 1391-1401.
Chikuma, S. et al., "Negative Regulation of T Cell Receptor-Lipid Raft Interaction by Cytotoxic T Lymphocyte—associated Antigen 4", The Journal of Experimental Medicine (2003), vol. 197(1), pp. 129-135.
Chikuma, S. et al., "B7-Independent Inhibition of T Cells by CTLA-4", The Journal of Immunology (2005), vol. 175(1), pp. 177-181.
Tivol, E. A. et al., "Loss of CTLA-4 leads to massive lymphoproliferation and fatal multiorgan tissue destruction, revealing a critical negative regulatory role of CTLA-4", Immunity (1995), vol. 3(5), pp. 541-547.
Gough, S. C. L. et al., "CTLA4 gene polymorphism and autoimmunity", Immunological Reviews (2005), vol. 204, pp. 102-115.
Carreno, B. M. et al., "CTLA-4 (CD152) Can Inhibit T Cell Activation by Two Different Mechanisms Depending on Its Level of Cell Surface Expression", The Journal of Immunology (2000), vol. 165(3), pp. 1352-1356.
Chai, J-G. et al., "CD152 Ligation by CD80 on T Cells Is Required for the Induction of Unresponsiveness by aostimulation-Deficient Antigen Presentation", The Journal of Immunology (2000), vol. 165(6), pp. 3037-3042.
Peggs, K. S. et al., "Blockade of CTLA-4 on both effector and regulatory T cell compartments contributes to the antitumor activity of anti-CTLA-4 antibodies", The Journal of Experimental Medicine (2009), vol. 206(8), pp. 1717-1725.
Quezada, S. A. et al., "CTLA4 blockade and GM-CSF combination immunotherapy alters the intratumor balance of affector and regulatory T cells", The Journal of Clinical Investigation (2006), vol. 116(7), pp. 1935-1945.
Curran, M. A. et al., "PD-1 and CTLA-4 combination blockade expands infiltrating T cells and reduces regulatory T and myeloid cells within B16 melanoma tumors", Proceedings of the National Academy of Sciences (2010), vol. 107 (9), pp. 4275-4280.
Perrin, P. J. et al., "CTLA-4 blockade enhances clinical disease and cytokine production during experimental allergic encephalomyelitis.", The Journal of immunology (1996), vol. 157(4), pp. 1333-1336.
Hurwitz, A. A. et al., "Specific blockade of CTLA-4/B7 interactions results in exacerbated clinical and histologic lisease in an actively-induced model of experimental allergic encephalomyelitis", Journal of Neuroimmunology (1997), vol. 73(1-2), pp. 57-62.
Leach, D. R. et al., "Enhancement of antitumor immunity by CTLA-4 blockade", Science (1996), vol. 271(5256), pp. 1734-1736.
Jure-Kunkel, M. N. et al., "Antitumor activity of anti-CTLA-4 monoclonal antibody (mAb) in combination with ixabepilone in preclinical tumor models", Journal of Clinical Oncology (2008), vol. 26(15), pp. 3048.

Saha, A. et aL, "Combination of CTL-associated antigen-4 blockade and depletion of CD25+ regulatory T cells enhance tumour immunity of dendritic cell-based vaccine in a mouse model of colon cancer", Scandinavian Journal of Immunology (2010), vol. 71(2), pp. 70-82.
Mokyr, M. B. et al., "Realization of the therapeutic potential of CTLA-4 blockade in low-dose chemotherapy-treated tmor-bearing mice", Cancer Research (1998), vol. 58(23), pp. 5301-5304.
Dewan, M. Z. et al., "Fractionated but not single-dose radiotherapy induces an immune-mediated abscopal effect when combined with anti-CTLA-4 antibody", Clinical Cancer Research (2009), vol. 15(17), pp. 5379-5388.
Davila, E. et al., "Generation of Antitumor Immunity by Cytotoxic T Lymphocyte Epitope Peptide Vaccination Vaccination, CpG-oligodeoxynucleotide Adjuvant, and CTLA-4 Blockade", Cancer Research (2003), vol. 63, pp. 3281-3288.
Takeda, K. et al., "Combination Therapy of Established Tumors by Antibodies Targeting Immune Activating and Suppressing Molecules", The Journal of Immunology (2010), vol. 184(10), pp. 5493-5501.
Redmond, W. L. et al., "Combined Targeting of Costimulatory (OX40) and Coinhibitory (CTLA-4) Pathways Elicits Potent Effector T Cells Capable of Driving Robust Antitumor Immunity", Cancer Immunology Research (2014), vol. 2 (2), pp. 142-153. Published Online First Nov. 11, 2013.
Waitz, R. et al., "Potent induction of tumor immunity by combining tumor cryoablation with anti-CTLA-4 therapy", Cancer Research (2012), vol. 72(2), pp. 430-439.
Keler, T. et al., "Activity and safety of CTLA-4 blockade combined with vaccines in cynomolgus macaques", The Journal of immunology (2003), vol. 171(11), pp. 6251-6259.
Hoos, A. et al., "Development of ipilimumab: Contribution to a new paradigm for cancer immunotherapy", Seminars in Oncology (2010), vol. 37(5), pp. 533-546.
Ascierto, P. A. et al., "Anti-CTLA4 monoclonal antibodies: the past and the future in clinical application", Journal of Translational Medicine (2011), vol. 9/1/196, p. 1-5.
Hodi, F. S. et al., "Improved survival with ipilimumab in patients with metastatic melanoma", The New England journal of medicine (2010), vol. 363(8), pp. 711-723.
Al-Lazikani, B. et al., "Standard conformations for the canonical structures of immunoglobulins", Journal of Molecular Biology (1997), vol. 273(4), pp. 927-948.
Chothia, C. et al., "Domain Association in Immunoglobulin Molecules. The packing of variable domains", Journal of Molecular Biology (1985), vol. 186(3), pp. 651-663.
Chothia, C. et al., "Canonical structures for the hypervariable regions of immunoglobulins", Journal of Molecular Thology (1987), vol. 196(4), pp. 901-917.
Chothia, C. et al., "Conformations of immunoglobulin hypervariable regions", Nature (1989), vol. 342(6252), pp. 877-883.
Huston, J. S. et al., "Protein engineering of antibody binding sites: recovery of specific activity in an anti-digoxin single-chain Fv analogue produced in *Escherichia coli*", Proceedings of the National Academy of Sciences of the United States of America (1988), vol. 85(16), pp. 5879-5883.
Riechmann, L. et al., "Single domain antibodies: comparison of camel VH and camelised human VH domains", Journal of Immunological Methods (1999), vol. 231(1-2), pp. 25-38.
Muyldermans, S. et al., "Single domain camel antibodies: current status", Reviews in Molecular Biotechnology (2001), vol. 74(4), pp. 277-302.
Hamers-Casterman, C. et al., "Naturally occurring antibodies devoid of light chains", Nature (1993), vol. 363 (6428), pp. 446-448.
Nguyen, V. K. et al., "Heavy-chain antibodies in Camelidae; a case of evolutionary innovation", Immunogenetics (2002), vol. 54(1), pp. 39-47.
Nguyen, V. K. et al., "Heavy-chain only antibodies derived from dromedary are secreted and displayed by mouse B cells", Immunology (2003), vol. 109(1), pp. 93-101.

(56) References Cited

OTHER PUBLICATIONS

Koch-Nolte, F. et al., "Single domain antibodies from llama effectively and specifically block T cell ecto-ADP- ribosyltransferase ART2.2 in vivo", The FASEB Journal (2007), vol. 21(13), pp. 3490-3498.

Holliger, P. et al., ""Diabodies": small bivalent and bispecific antibody fragments", Proceedings of the National Academy of Sciences (1993), vol. 90(14), pp. 6444-6448.

Higgins, D.G. et al., "Using CLUSTAL for Multiple Sequence Alignments", Methods in Enzymology(1996), vol. 266, pp. 383-402.

Larkin, M. A. et al., "Clustal W and Clustal X version 2.0", Bioinformatics (2007), vol. 23(21), pp. 2947-2948.

Graham, F. L. et al., "Characteristics of a Human Cell Line Transformed by DNA from Human Adenovirus Type 5", J. Gen Virol(1977), vol. 36, pp. 59-72.

Urlaub, G. et al., "Isolation of Chinese hamster cell mutants deficient in dihydrofolate reductase activity", Proceedings of the National Academy of Sciences of the United States of America (1980), vol. 77(7), pp. 4216-4220.

Mather, J. P. et al., "Establishment and Characterization of Two Distinct Mouse Testicular Epithelial Cell Lines", Biology of Reproduction (1980), vol. 23(1), pp. 243-252.

Mather, J. P. et al., "Culture of Testicular Cells in Hormone-Supplemented Serum-Free Medium", Annals New York Academy of Sciences (1982), vol. 383(1), pp. 44-68.

International Search Report dated Jan. 22, 2018 in corresponding International Patent Application No. PCT/EP2017/075329.

International Preliminary Report on Patentability dated Apr. 18, 2019 in corresponding International Patent Application No. PCT/EP2017/075329.

Kuraoka, M. et al., "KU257259.1", GenBank, Mar. 10, 2016 (Mar. 10, 2016), see the nucleotide sequence.

Mylvaganam et al., "X60684.1", GenBank, Jul. 26, 2016 (Jul. 26, 2016), see the nucleotide sequence.

The International Search Report for PCT/CN2016/101681.

\* cited by examiner

EC50 of CTLA4 Antibody Binding with CTLA4 by Elisa

EC50 of CTLA4 Antibody Binding with CTLA4 by FACS

ANTI-CTLA4 ANTIBODIES

FIELD OF THE INVENTION

The present disclosure generally relates to novel anti-CTLA4 antibodies.

REFERENCE TO SEQUENCE LISTING

This application contains the sequences shown in table below. A computer readable copy of the Sequence Listing is submitted along with this application, which is incorporated herein by reference.

| SEQ ID NO | Annotation |
|---|---|
| 1 | Peptide sequence of heavy chain variable region of 6F3 |
| 2 | Nucleotide sequence of heavy chain variable region of 6F3 |
| 3 | Peptide sequence of heavy chain CDR1 of 6F3 |
| 4 | Nucleotide sequence of heavy chain CDR1 of 6F3 |
| 5 | Peptide sequence of heavy chain CDR2 of 6F3 |
| 6 | Nucleotide sequence of heavy chain CDR2 of 6F3 |
| 7 | Peptide sequence of heavy chain CDR3 of 6F3 |
| 8 | Nucleotide sequence of heavy chain CDR3 of 6F3 |
| 9 | Peptide sequence of light chain variable region of 6F3 |
| 10 | Nucleotide sequence of light chain variable region of 6F3 |
| 11 | Peptide sequence of light chain CDR1 of 6F3 |
| 12 | Nucleotide sequence of light chain CDR1 of 6F3 |
| 13 | Peptide sequence of light chain CDR2 of 6F3 |
| 14 | Nucleotide sequence of light chain CDR2 of 6F3 |
| 15 | Peptide sequence of light chain CDR3 of 6F3 |
| 16 | Nucleotide sequence of light chain CDR3 of 6F3 |
| 17 | Peptide sequence of heavy chain variable region of 10B10 |
| 18 | Nucleotide sequence of heavy chain variable region of 10B10 |
| 19 | Peptide sequence of heavy chain CDR1 of 10B10 |
| 20 | Nucleotide sequence of heavy chain CDR1 of 10B10 |
| 21 | Peptide sequence of heavy chain CDR2 of 10B10 |
| 22 | Nucleotide sequence of heavy chain CDR2 of 10B10 |
| 23 | Peptide sequence of heavy chain CDR3 of 10B10 |
| 24 | Nucleotide sequence of heavy chain CDR3 of 10B10 |
| 25 | Peptide sequence of light chain variable region of 10B10 |
| 26 | Nucleotide sequence of light chain variable region of 10B10 |
| 27 | Peptide sequence of light chain CDR1 of 10B10 |
| 28 | Nucleotide sequence of light chain CDR1 of 10B10 |
| 29 | Peptide sequence of light chain CDR2 of 10B10 |
| 30 | Nucleotide sequence of light chain CDR2 of 10B10 |
| 31 | Peptide sequence of light chain CDR3 of 10B10 |
| 32 | Nucleotide sequence of light chain CDR3 of 10B10 |
| 33 | Peptide sequence of heavy chain variable region of humanized 6F3 |
| 34 | Nucleotide sequence of heavy chain variable region of humanized 6F3 |
| 35 | Peptide sequence of light chain variable region of humanized 6F3 |
| 36 | Nucleotide sequence of light chain variable region of humanized 6F3 |
| 37 | Peptide sequence of heavy chain variable region of humanized 10B10 |
| 38 | Nucleotide sequence of heavy chain variable region of humanized 10B10 |
| 39 | Peptide sequence of light chain variable region of humanized 10B10 |
| 40 | Nucleotide sequence of light chain variable region of humanized 10B10 |
| 41 | Peptide sequence of heavy chain of humanized 6F3 |
| 42 | Nucleotide sequence of heavy chain of humanized 6F3 |
| 43 | Peptide sequence of light chain of humanized 6F3 |
| 44 | Nucleotide sequence of light chain of humanized 6F3 |
| 45 | Peptide sequence of heavy chain of humanized 10B10 |
| 46 | Nucleotide sequence of heavy chain of humanized 10B10 |
| 47 | Peptide sequence of light chain of humanized 10B10 |
| 48 | Nucleotide sequence of light chain of humanized 10B10 |
| 49 | Nucleotide sequence of human CTLA4-His |
| 50 | Peptide sequence of human CTLA4-His |
| 51 | Nucleotide sequence of human CTLA4-mFc |
| 52 | Peptide sequence of human CTLA4-mFc |
| 53 | Nucleotide sequence of human CTLA4-hFc |
| 54 | Peptide sequence of human CTLA4-hFc |

BACKGROUND

Two distinct signals are required for the activation of T cells. The first is an antigen-specific interaction between the T cell receptor (TCR) and nominal antigen presented in the context of the MHC on the surface of an antigen-presenting cells (APCs). The second signal is provided through a number of potential co-stimulatory molecules. The activation of T cell is tightly regulated by multiple mechanisms, including cell surface proteins which expand or downregulate T cell responses (Bretscher et al., (1970) Science 69: 1042; Bernard et al., (2002) Transplantation 73: S31-S35). CD28, a constitutively expressed Ig-family protein, is one of the best-characterized co-stimulatory signals for T cell response. CD28 binding to ligands CD80 (B7-1) and CD86 (B7-2) on APCs leads to T cell proliferation by inducing production of interleukin-2 (IL-2) and anti-apoptotic factors. CTLA4 is the first molecule identified as a co-inhibitory molecule and play an important role in regulating both humoral and cellular immune response (Brunet et al., (1987) Nature 328:267-270). CTLA4 belongs to CD28 superfamily with 31% overall amino acid identity to CD28. CTAL4 is composed of disulfide-linked homodimers of extracellular IgV domains. (Stamper et al., (2001) Nature 410: 608-611). Unlike other inhibitory receptors, CTLA4 lacks a classic immunoreceptor tyrosine-based inhibitory motif (ITIM). Despite this, two phosphatases, SHP-2 and the serine-threonine phosphatase protein phosphatase 2A (PP2A), have been reported to associate with the YVKM motif of CTLA4 (Rudd et al., (2009) Immunol Rev. 229: 12-26). CD28 and CTLA4 share CD80 and CD86 as their natural ligands. However, the affinity of the CTLA4:B7 interaction is over 10 times higher than the affinity of the CD28:B7 interaction (Peach et al., (1994) J Exp Med 180:2049-2058). This allows CTLA4 to sequester B7 ligands from CD28 and antagonize CD28-dependent costimulation, which account for part of the inhibitory effect of CTLA4 on T cell activation. CTLA4 has also been proposed to deliver distinct distal signals independent of the TCR signal to attenuate T cell responses (Calvo et al., (1997) J Exp Med 186: 1645-1653). By interacting with the B7 molecules on APCs, CTLA4 induces the expression of IDO, which catalyzes the conversion of tryptophan to kynurenine, resulting in a local tryptophan depletion and subsequent inhibition of T cell proliferation and activation (Mellor et al., (2004) Int Immunol 16: 1391-1401). Lipid raft-associated CTLA4 interacted intimately with the TCR complex and altered lipid raft integrity and TCR-mediated signals (Chikuma et al., (2003) J Exp Med 197: 129-135). In addition, CTLA4 can function independent of B7 ligation as a consequence of recruitment to the synapse on activated T cells (Chikuma et al., (2005) J Immunol 175: 177-181).

The importance of CTLA4 as a negative regulator is dramatically revealed through the phenotype of CTLA4 knockout mice (Tivol et al., (1995) Immunity 3:541-547).

CTLA4 deficient mice develop a massive and rapidly lethal T-lymphoproliferative disease with splenomegaly, lymphadenopathy and multiorgan T-lymphocytic infiltration, resulting from excessive proliferation of T cells following recognition of antigen and unopposed or uncompeted co-stimulatory interactions between CD80/CD86 and CD28. In addition, polymorphisms in the CTLA4 gene are linked with several autoimmune diseases (Gough et al., (2005) Immunol Rev 204:102-15), including type 1 diabetes, thyroiditis, systemic lupus erythematosus, and rheumatoid arthritis.

While CD28 is expressed on most resting and activated T cells, CTLA4 is restricted to activated T cells, except in the case of regulatory T cells (Treg) where it is expressed constitutively. CTLA4 functions on both Treg and CD8 effector cells (Teff). CTLA4 targets the transcription factor Eomes in the regulation of CD8+ effector function, and results in reduced IFNγ and Granzyme B expression and potential cytolytic T-cell function. Loss of CTLA4 expression on Treg cells impairs their suppressive function and elicit pathological autoimmunity. The inhibitory effect on Teff and the stimulatory effect on Treg of CTLA4 lead to attenuated immune responses, and thus mediates tolerance and/or anergy (Carreno et al., (2000) J Immunol 165: 1352-1356; Chai et al., (2000) J Immunol 165: 3037-3042).

CTLA4 has been found to have a correlation with cancer growth and development due to its negative role in immune response. CTLA4 is expressed in tumors at higher levels on Treg cells as compared with intra-tumoral Teff cell, and it has been shown that anti-CTLA4 needs to bind to Treg cells and to Teff cells to induce full tumor protection (Peggs et al., (2009) J Exp Med 206: 1717). Furthermore, anti-CTLA4-mediated tumor destruction was regularly associated with an increased ratio of intra-tumoral CD4+ Teff/Treg cells and an increased ratio of intra-tumoral CD8+ Teff/Treg cells (Quezada et al., (2006) J Clin Invest 116: 1935; Curran et al., (2010) Proc Natl Acad Sci USA 107: 4275).

In early studies with animal models, antibody blockade of CTLA4 was shown to exacerbate autoimmunity (Perrin et al., (1996) J Immunol 157: 1333-6; Hurwitz et al., (1999) J Neuroimmunol 73: 57-62). By extension to tumor immunity, blockade of the CTLA4 inhibitory signal was accordingly shown to enhance tumor-specific T-cell immunity and cause regression of established tumors. In a murine model of aggressive colon cancer, for example, Leach et al. demonstrated the therapeutic efficacy of CTLA4 blockade. Administration of CTLA4 directed antibody significantly rejected tumor growth of both CD80 positive and CD80 negative colon carcinoma. Furthermore, this rejection resulted in immunity to a secondary exposure to tumor cells. Additionally, the authors showed that treatment with anti-CTLA4 also reduced the growth of the murine fibrosarcoma Sa1N (Leach et al., (1996) Science 271: 1734-1736). Recent studies suggested that direct enhancement of Teff cell function and concomitant inhibition of Treg cell activity through blockade of CTLA4 on both cell types is essential for mediating the full therapeutic effects of anti-CTLA4 antibodies during cancer immunotherapy (Peggs et al., (2009) J Exp Med 206:1717-25).

The versatility of CTLA4 blockade, in combination with multiple therapeutic interventions, has been reported in a variety of mouse tumor models, such as 4T1 (breast cancer), EL4 (lymphoma), CT26 (colon cancer) (Jure-Kunkel et al., (2008) J Clin Oncol 26 Suppl 15: 3048). Synergistic effects on anti-tumor activity have been demonstrated in combination with vaccines (Saha et al., (2010) Scand J Immunol 71: 70-82), chemotherapy (Mokyr et al., (1998) Cancer Res 58: 5301-5304), radiation (Dewan et al., (2009) Clin Cancer Res 15: 5379-5388), cytosine-phosphateguanine oligodeoxy-nucleotides (CpG-ODN) adjuvants (Davila et al., (2003) Cancer Res 63: 3281-3288), antibodies (Takeda et al., (2010) J Immunol 184: 5493-5501; Redmond et al., (2013) Cancer Immunol Res 2: 142-53) and cryoablation (Waitz et al., (2012) Cancer Res 72: 430-439.). For an example, using 3 different tumor lines: SAIN fibrosarcoma, M109 lung carcinoma and EMT-6 mammary carcinoma, Jure-Kunkel et al demonstrated that the combination of the anti-CTLA4 antibody and ixabepilone showed a synergistic antitumor effect in these tumor models achieving long-lasting complete responses in 70-100% of the animals, which yielded much superior efficacy compared to each treatment alone. When animals with complete tumor regressions were rechallenged with a lethal dose of tumor cells, animals treated with ixabepilone plus CTLA4 antibody rejected a subsequent tumor, indicating the development of a protective memory immune response (Jure-Kunkel et al., (2008) J Clin Oncol 26 Suppl 15: 3048).

Ipilimumab, a human anti-CTLA4 antibody capable to block CTLA4/B7 interactions (Keler et al., (2003) J Immunol 171: 6251-9) has been tested in a variety of clinical trials for multiple malignancies (Hoos et al., (2010) Semin Oncol 37: 533-46; Ascierto et al., (2011) J Transl Med 9: 196). Tumor regressions and disease stabilization were frequently observed, and accompanied by adverse events with inflammatory infiltrates capable of affecting a variety of organ systems. In 2011, ipilimumab, was approved for the treatment of unresectable or metastatic melanoma in the United States and European Union based on an improvement in overall survival in a phase III trial of previously treated patients with advanced melanoma (Hodi et al., (2010) N Engl J Med 363: 711-23).

Ipilimumab treatment, however, has been associated with severe and potentially fatal immunological adverse effects due to T cell activation and proliferation in 10-20% of people being treated. The cost of ipilimumab treatment is staggering high. Therefore, there is continuing need to develop novel antibodies against CTLA4.

BRIEF SUMMARY OF THE INVENTION

In one aspect, the present disclosure provides novel antibodies or antigen binding fragments thereof that bind to CTLA4, polynucueotides encoding the same, and methods of using the same.

In one embodiment, the antibodies or fragments thereof bind to human CTLA4. In another embodiment, the antibodies or fragments thereof bind to human and to cynomolgous CTLA4. In another embodiment, the antibodies or fragments thereof block the interaction of CTLA4 on T cells with its ligand CD80 and CD86.

In certain embodiments, the antibodies or antigen-binding fragments thereof comprise a heavy chain CDR sequence selected from the group consisting of: SEQ ID NOs: 3, 5, 7, 19, 21, and 23.

In certain embodiments, the antibodies or antigen-binding fragments thereof comprises a light chain CDR sequence selected from the group consisting of: SEQ ID NOs: 11, 13, 15, 27, 29 and 31.

In certain embodiments, the antibodies or antigen-binding fragments thereof comprise a heavy chain variable region selected from the group consisting of:
  a) a heavy chain variable region comprising SEQ ID NO: 3, SEQ ID NO: 5, and/or SEQ ID NO: 7; and
  b) a heavy chain variable region comprising SEQ ID NO: 19, SEQ ID NO: 21, and/or SEQ ID NO: 23.

In certain embodiments, the antibodies or antigen-binding fragments thereof comprise a light chain variable region selected from the group consisting of:
 a) a light chain variable region comprising SEQ ID NO: 11, SEQ ID NO: 13, and/or SEQ ID NO: 15; and
 b) a light chain variable region comprising SEQ ID NO: 27, SEQ ID NO: 29, and/or SEQ ID NO: 31.

In certain embodiments, the antibodies or antigen-binding fragments thereof comprise:
 a) a heavy chain variable region comprising SEQ ID NO: 3, SEQ ID NO: 5, and/or SEQ ID NO: 7; and a light chain variable region comprising SEQ ID NO: 11, SEQ ID NO: 13, and/or SEQ ID NO: 15; or
 b) a heavy chain variable region comprising SEQ ID NO: 19, SEQ ID NO: 21, and/or SEQ ID NO: 23; and a light chain variable region comprising SEQ ID NO: 27, SEQ ID NO: 29, and/or SEQ ID NO: 31.

In certain embodiments, the antibodies or antigen-binding fragments thereof comprise a heavy chain variable region selected from the group consisting of: SEQ ID NO: 1, SEQ ID NO: 17, SEQ ID NO: 33, SEQ ID NO: 37 and the homologue sequences of at least 80% (e.g. at least 85%, 88%, 90%, 91%, 92%, 93%, 94%, 95%, 96%, 97%, 98%, 99%) sequence identity thereof.

In certain embodiments, the antibodies or antigen-binding fragments thereof comprise a light chain variable region selected from the group consisting of: SEQ ID NO: 9, SEQ ID NO: 25, SEQ ID NO: 35, SEQ ID NO: 39 and the homologue sequences of at least 80% (e.g. at least 85%, 88%, 90%, 91%, 92%, 93%, 94%, 95%, 96%, 97%, 98%, 99%) sequence identity thereof.

In certain embodiments, the antibodies or antigen-binding fragments thereof comprise:
 a) a heavy chain variable region comprising SEQ ID NO: 1 and a light chain variable region comprising SEQ ID NO: 9;
 b) a heavy chain variable region comprising SEQ ID NO: 17 and a light chain variable region comprising SEQ ID NO: 25;
 c) a heavy chain variable region comprising SEQ ID NO: 33 and a light chain variable region comprising SEQ ID NO: 35;
 d) a heavy chain variable region comprising SEQ ID NO: 37 and a light chain variable region comprising SEQ ID NO: 39;
 e) a heavy chain variable region and a light chain variable region of at least 80% sequence identity to a), b), c) or d).

In certain embodiments, the antibodies or antigen-binding fragments thereof are capable of specifically binding to human cytotoxic T-lymphocyte-associated protein 4 (CTLA4) protein at a KD value no more than $10^{-9}$ M (e.g., $\leq 9\times 10^{-10}$ M, $\leq 8\times 10^{-10}$ M, $\leq 7\times 10^{-10}$ M, $\leq 6\times 10^{-10}$ M, $\leq 5\times 10^{-10}$ M, $\leq 4\times 10^{-10}$ M, $\leq 3\times 10^{-10}$ M, $\leq 2\times 10^{-10}$ M, or $\leq 10^{-10}$ M) as measured by surface plasmon resonance binding assay.

In certain embodiments, the antibodies or antigen-binding fragments thereof bind to monkey CTLA4 at a KD value no more than $10^{-8}$ M (e.g., $\leq 9\times 10^{-9}$ M, $\leq 8\times 10^{-9}$ M, $\leq 7\times 10^{-9}$ M, $\leq 6\times 10^{-9}$ M, $\leq 5\times 10^{-9}$ M, $\leq 4\times 10^{-9}$ M, $\leq 3\times 10^{-9}$ M, $\leq 2\times 10^{-9}$ M, or $\leq 10^{-9}$ M), or no more than $10^{-9}$ M (e.g., no more than $\leq 9\times 10^{-10}$ M, $\leq 8\times 10^{-10}$ M, $\leq 7\times 10^{-10}$ M, $\leq 6\times 10^{-10}$ M, $\leq 5\times 10^{-10}$ M, $\leq 4\times 10^{-10}$ M, $\leq 3\times 10^{-10}$ M, $\leq 2\times 10^{-10}$ M, or $\leq 10^{-10}$ M).

In certain embodiments, the antibodies or antigen-binding fragments thereof are capable of inhibiting binding of human CTLA4 to its ligand at an IC50 of no more than 600 ng/ml (e.g., ≤500 ng/ml, ≤400 ng/ml, ≤300 ng/ml, ≤200 ng/ml, ≤100 ng/ml) as measured by ELISA assay.

In certain embodiments, the antibodies or antigen-binding fragments thereof are capable of binding to human CTLA4 at an EC50 of no more than 30 ng/ml (e.g., ≤25 ng/ml, ≤20 ng/ml, ≤15 ng/ml, ≤10 ng/ml, ≤9 ng/ml, ≤8 ng/ml, ≤7 ng/ml, ≤6 ng/ml, ≤5 ng/ml, ≤4 ng/ml, ≤3 ng/ml, ≤2 ng/ml, ≤1 ng/ml) measured by ELISA assay.

In certain embodiments, the antibodies or antigen-binding fragments thereof are capable of inhibiting binding of human CTLA4 to its ligand at an IC50 of no more than 600 ng/ml (e.g., ≤500 ng/ml, ≤400 ng/ml, ≤300 ng/ml, ≤200 ng/ml, ≤100 ng/ml) or no more than 30 ng/ml (e.g., ≤25 ng/ml, ≤20 ng/ml, ≤15 ng/ml, ≤10 ng/ml, ≤9 ng/ml, ≤8 ng/ml, ≤7 ng/ml, ≤6 ng/ml, ≤5 ng/ml, ≤4 ng/ml, ≤3 ng/ml, ≤2 ng/ml, ≤1 ng/ml) as measured by FACS assay.

The antibody or antigen-binding fragment thereof of any of the preceding claims, capable of binding to human CTLA4 at an EC50 of no more than 6000 ng/ml, no more than 2400 ng/ml, 1200 ng/ml or no more than 400 ng/ml measured by FACS assay.

In certain embodiments, the antibodies or antigen-binding fragments thereof are humanized monoclonal antibodies.

In certain embodiments, the antibodies or antigen-binding fragments thereof are produced by a host cell.

In another aspect, the present disclosure provides antibodies or antigen-binding fragments thereof that compete for the same epitope with the antibodies or the antigen binding fragments thereof disclosed herein.

In certain embodiments, the antibodies or antigen-binding fragments thereof are a camelized single domain antibody, a diabody, a scFv, an scFv dimer, a BsFv, a dsFv, a (dsFv)2, a dsFv-dsFv', an Fv fragment, a Fab, a Fab', a F(ab')2, a disulfide stabilized diabody (ds diabody), a nanobody, a domain antibody, or a bivalent domain antibody.

In certain embodiments, the antibodies or antigen-binding fragments thereof further comprise a conjugate.

The present disclosure further provides an isolated polynucleotide encoding the antibody or an antigen binding fragment thereof provided herein. The present disclosure further provides a vector comprising said isolated polynucleotide. The present disclosure further provides a host cell comprising said vector. In certain embodiments, the polynucleotides provided herein are operably associated with a promoter such as a SV40 promoter in a vector. In certain embodiments, host cells comprising the vectors provided herein are Chinese hamster ovary cell, or 293F cell.

In another aspect, the present disclosure provides a method of expressing the antibodies or antigen-binding fragments thereof disclosed herein. In certain embodiments, the method comprises culturing a host cell under the condition at which the polynucleotide encoding the antibodies or antigen-binding fragments thereof is expressed.

In another aspect, the present disclosure provides a kit comprising the antibodies or antigen-binding fragments thereof as disclosed herein.

In another aspect, the present disclosure provides a method of treating a diseased mediated by CTLA4 in an individual. In certain embodiments, the method comprises administering a therapeutically effective amount of the antibody or antigen-binding fragment thereof as disclosed herein to the individual. In certain embodiments, the individual has been identified as having a disorder or a condition likely to respond to a CTLA4 inhibitor. In certain embodiments, the disease is cancer.

In another aspect, the present disclosure provides a pharmaceutical composition comprising the antibody or antigen-binding fragment thereof as disclosed herein and one or more pharmaceutically acceptable carriers. In certain of these embodiments, the pharmaceutical carriers may be, for example, diluents, antioxidants, adjuvants, excipients, or non-toxic auxiliary substances.

DETAILED DESCRIPTION OF THE INVENTION

Figure 1:
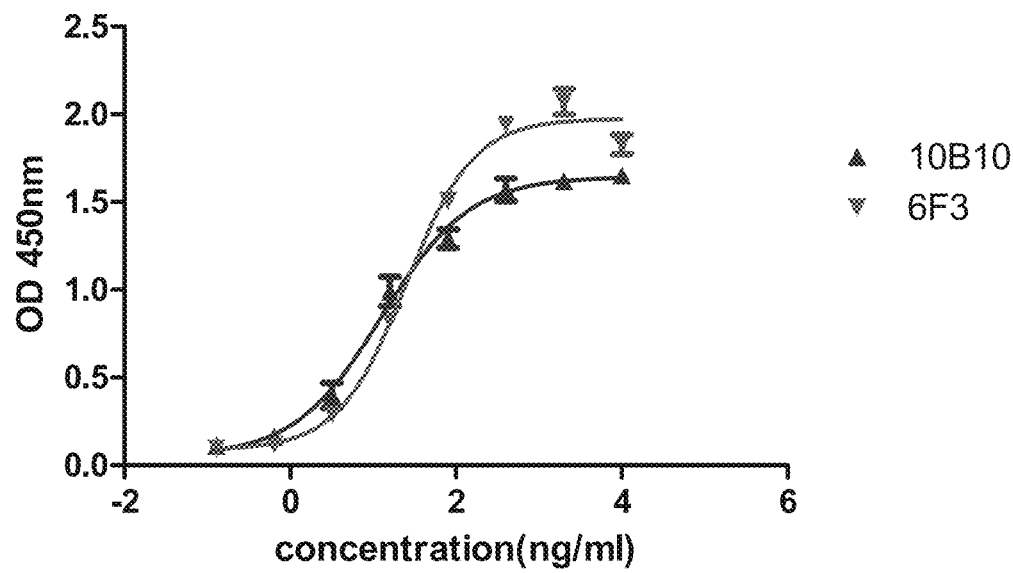
FIG. 1 is the graph showing the binding EC50 of murine antibody 6F3 and 10B10 as measured by ELISA. The top panel of the figure shows the absorbance over a range of concentrations of murine antibodies, and the bottom panel of the figure shows the calculated EC50 of each of the test antibodies.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multispecific antibody, or bispecific (bivalent) antibody that binds to a specific antigen. A native intact antibody comprises two heavy chains and two light chains. Each heavy chain consists of a variable region and a first, second, and third constant region, while each light chain consists of a variable region and a constant region. Mammalian heavy chains are classified as α, δ, ε, γ, and µ, and mammalian light chains are classified as λ or κ. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variables region in both chains generally contain three highly variable loops called the complementarity determining regions (CDRs) (light (L) chain CDRs including LCDR1, LCDR2, and LCDR3, heavy (H) chain CDRs including HCDR1, HCDR2, HCDR3). CDR boundaries for the antibodies and antigen-binding fragments disclosed herein may be defined or identified by the conventions of Kabat, Chothia, or Al-Lazikani (Al-Lazikani, B., Chothia, C., Lesk, A. M., J Mol Biol 273(4): 927 (1997); Chothia, C. et al., J Mol Biol 186(3):651-63 (1985); Chothia, C. and Lesk, A. M., J Mol Biol, 196:901 (1987); Chothia, C. et al., Nature 342 (6252):877-83 (1989); Kabat E. A. et al., National Institutes of Health, Bethesda, Md. (1991)). The three CDRs are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment formed from a portion of an antibody comprising one or more CDRs, or any other antibody fragment that binds to an antigen but does not comprise an intact native antibody structure. Examples of antigen-binding fragment include, without limitation, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, and a bivalent domain antibody. An antigen-binding fragment is capable of binding to the same antigen to which the parent antibody binds. In certain embodiments, an antigen-binding fragment may comprise one or more CDRs from a particular human antibody grafted to a framework region from one or more different human antibodies.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab'.

"Fc" with regard to an antibody refers to that portion of the antibody consisting of the second and third constant regions of a first heavy chain bound to the second and third constant regions of a second heavy chain via disulfide bonding. The Fc portion of the antibody is responsible for various effector functions such as ADCC, and CDC, but does not function in antigen binding.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Huston J S et al. Proc Natl Acad Sci USA, 85:5879(1988)). "Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann L. and Muyldermans S., J Immunol Methods 231(1-2):25-38 (1999); Muyldermans S., J Biotechnol 74(4):277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., Nature 363(6428):446-8 (1993); Nguyen V K. et al. Immunogenetics 54(1):39-47 (2002); Nguyen V K. et al., Immunology 109(1):93-101 (2003)). The variable domain of a heavy chain antibody (VHH domain) represents the smallest known antigen-binding unit generated by adaptive immune responses (Koch-Nolte F. et al., FASEB J 21(13):3490-8. (2007)).

A "nanobody" refers to an antibody fragment that consists of a VHH domain from a heavy chain antibody and two constant domains, CH2 and CH3.

"Diabodies" include small antibody fragments with two antigen-binding sites, wherein the fragments comprise a $V_H$ domain connected to a $V_L$ domain in the same polypeptide chain ($V_H$-$V_L$ or $V_L$-$V_H$) (see, e.g., Holliger P. et al., Proc Natl Acad Sci USA. 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same of different antigens (or epitopes).

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

In certain embodiments, a "(dsFv)$_2$" comprises three peptide chains: two $V_H$ moieties linked by a peptide linker and bound by disulfide bridges to two $V_L$ moieties.

In certain embodiments, a "bispecific ds diabody" comprises $V_{H1}$-$V_{L2}$ (linked by a peptide linker) bound to $V_{L1}$-$V_{H2}$ (also linked by a peptide linker) via a disulfide bridge between $V_{H1}$ and $V_{L1}$.

In certain embodiments, a "bispecific dsFv" or dsFv-dsFv'" comprises three peptide chains: a $V_{H1}$-$V_{H2}$ moiety wherein the heavy chains are linked by a peptide linker (e.g., a long flexible linker) and bound to $V_{L1}$ and $V_{L2}$ moieties, respectively, via disulfide bridges, wherein each disulfide paired heavy and light chain has a different antigen specificity.

In certain embodiments, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'S of the other moiety and form two binding sites which can target the same antigens (or eptipoes) or different antigens (or eptipoes). In other embodiments, an "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

The term "humanized" as used herein, with reference to antibody or antigen-binding fragment, means that the antibody or the antigen-binding fragment comprises CDRs derived from non-human animals, FR regions derived from human, and when applicable, the constant regions derived from human. A humanized antibody or antigen-binding fragment is useful as human therapeutics in certain embodiments because it has reduced immunogenicity in human. In some embodiments, the non-human animal is a mammal, for example, a mouse, a rat, a rabbit, a goat, a sheep, a guinea pig, or a hamster. In some embodiments, the humanized antibody or antigen-binding fragment is composed of substantially all human sequences except for the CDR sequences which are non-human. In some embodiments, the FR regions derived from human may comprise the same amino acid sequence as the human antibody from which it is derived, or it may comprise some amino acid changes, for example, no more than 10, 9, 8, 7, 6, 5, 4, 3, 2, or 1 changes of amino acid. In some embodiments, such change in amino acid could be present in heavy chain FR regions only, in light chain FR regions only, or in both chains. In some preferable embodiments, the humanized antibodies comprise human FR1-3 and human JH and Jκ.

The term "chimeric" as used herein, means an antibody or antigen-binding fragment, having a portion of heavy and/or light chain derived from one species, and the rest of the heavy and/or light chain derived from a different species. In an illustrative example, a chimeric antibody may comprise a constant region derived from human and a variable region from a non-human species, such as from mouse.

"CTLA4" as used herein refers to Cytotoxic T-lymphocyte-associated antigen 4, a transmembrane protein and expressed mainly on the surface of activated Treg cell. CTLA4 is a homologue of CD28 that binds CD80 (B7-1) and CD86 (B7-2) (both are expressed on antigen presenting cell (APC)) with higher affinity. While co-stimulatory pathway of cell-mediated immunity, i.e. CD28 binds CD80 (B7-1) and CD86 (B7-2) on the surface of the T-cell, plays a role in T-cell activation, differentiation, tissue migration and peripheral tolerance induction (See Salomon et al., 2001, Ann Rev Immunol 19:225.), competitive binding of CTLA4 to CD80/86 result in blocking of CD80/86-CD28 interaction and terminating T cell activation. Representative amino acid sequence of human CTLA4 is disclosed under the GenBank accession number: AAL07473.1, and the representative mRNA nucleic acid sequence encoding the human CTLA4 is shown under the GenBank accession number: AF414120.1.

The term "specific binding" or "specifically binds" as used herein refers to a non-random binding reaction between two molecules, such as for example between an antibody and an antigen. In certain embodiments, the antibodies or antigen-binding fragments provided herein specifically bind human and/or CTLA4 with a binding affinity ($K_D$) of $\leq 10^{-6}$ M (e.g., $\leq 5 \times 10^{-7}$ M, $\leq 2 \times 10^{-7}$ M, $\leq 10^{-7}$ M, $\leq 5 \times 10^{-8}$ M, $\leq 2 \times 10^{-8}$ M, $\leq 10^{-8}$ M, $\leq 5 \times 10^{-9}$ M, $\leq 2 \times 10^{-9}$ M, $\leq 10^{-9}$ M, $10^{-10}$ M). $K_D$ as used herein refers to the ratio of the dissociation rate to the association rate ($k_{off}/k_{on}$), may be determined using surface plasmon resonance methods for example using instrument such as Biacore.

The ability to "block binding" or "compete for the same epitope" as used herein refers to the ability of an antibody or antigen-binding fragment to inhibit the binding interaction between two molecules (e.g. human CTLA4 and an anti-CTLA4 antibody) to any detectable degree. In certain embodiments, an antibody or antigen-binding fragment that blocks binding between two molecules inhibits the binding interaction between the two molecules by at least 50%. In certain embodiments, this inhibition may be greater than 60%, greater than 70%, greater than 80%, or greater than 90%.

The term "epitope" as used herein refers to the specific group of atoms or amino acids on an antigen to which an antibody binds. Two antibodies may bind the same epitope within an antigen if they exhibit competitive binding for the antigen. For example, if an antibody or antigen-binding fragment as disclosed herein blocks binding of the exemplary antibodies such as 6F3 and 10B10 to human CTLA4, then the antibody or antigen-binding fragment may be considered to bind the same epitope as those exemplary antibodies.

"6F3" or "6F3 murine" as used herein refers to a mouse monoclonal antibody having heavy chain CDR1 of SEQ ID NO: 3, CDR2 of SEQ ID NO:5 and CDR3 of SEQ ID NO:7, and light chain CDR1 of SEQ ID NO: 11, CDR2 of SEQ ID NO: 13 and CDR3 of SEQ ID NO: 15.

"6F3 humanized" as used herein refers to a humanized monoclonal antibody of 6F3 and has a heavy chain variable region of SEQ ID NO: 33 and light chain variable region of SEQ ID NO: 35.

"10B10" or "10B10 murine" as used herein refers to a mouse monoclonal antibody having heavy chain CDR1 of SEQ ID NO: 19, CDR2 of SEQ ID NO:21 and CDR3 of SEQ ID NO:23, and light chain CDR1 of SEQ ID NO:27, CDR2 of SEQ ID NO:29 and CDR3 of SEQ ID NO: 31.

"10B10 humanized" as used herein refers to a humanized monoclonal of 10B10 and has a heavy chain variable region of SEQ ID NO: 37 and light chain variable region of SEQ ID NO: 39.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. In certain embodiments, the antibodies and antigen-binding fragments have a purity of at least 90%, 93%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating.

The phrase "host cell" as used herein refers to a cell into which an exogenous polynucleotide and/or a vector has been introduced.

The term "therapeutically effective amount" or "effective dosage" as used herein refers to the dosage or concentration of a drug effective to treat a disease or condition responsible to CTLA4 antibody.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Anti-CTLA4 Antibody

The CDR sequences and heavy or light chain variable region sequences of anti-CTLA3 antibodies 6F3, 10B10, 6F3 humanized and 10B10 humanized are shown in Table 1-4 below.

TABLE 1

Amino Acid SEQ ID NOs

| | AMINO ACID SEQ ID NOs | | | | | | | |
|---|---|---|---|---|---|---|---|---|
| Antibody | HCVR | HCDR1 | HCDR2 | HCDR3 | LCVR | LCDR1 | LCDR2 | LCDR3 |
| 6F3 | 1 | 3 | 5 | 7 | 9 | 11 | 13 | 15 |
| 10B10 | 17 | 19 | 21 | 23 | 25 | 27 | 29 | 31 |
| 6F3 Hu | 33 | 3 | 5 | 7 | 35 | 11 | 13 | 15 |
| 10B10 Hu | 37 | 19 | 21 | 23 | 39 | 27 | 29 | 31 |

TABLE 2

Heavy chain CDR sequences

| Name | HCDR | SEQ ID NO | Sequence |
|---|---|---|---|
| 6F3 | 1 | 3 | DYEMH |
| | 2 | 5 | VIDPETGGITYNQKFKG |
| | 3 | 7 | RGARATVYNYVMDY |
| 10B10 | 1 | 19 | SGYSWN |
| | 2 | 21 | YIRFDGNNNYNPFLKN |
| | 3 | 23 | NGYTWGAMDF |

TABLE 3

Light Chain CDR sequences

| Name | LCDR | SEQ ID NO | Sequence |
|---|---|---|---|
| 6F3 | 1 | 11 | RASENIHNYLA |
| | 2 | 13 | NAKTLGD |
| | 3 | 15 | QHFWSTPWT |
| 10B10 | 1 | 27 | KTSQDINKYMA |
| | 2 | 29 | YTSILQP |
| | 3 | 31 | QQYDNLNT |

TABLE 4

Heavy chain and light chain variable region and full length sequences

| Name | Region[1] | SEQ ID NO | Sequence |
|---|---|---|---|
| 6F3 murine | Heavy chain variable | 1 | QVKLQESGAELVRPGASVTLSCKASGYTFTDYEMHWMKQTPVHGLE WIGVIDPETGGITYNQKFKGKATLTADKSSSTAYMEFLSLTSEDSA VYYCTRRGARATVYNYVMDYWGQGTSVTVSS |
| 6F3 murine | Light chain variable | 9 | DIVMTQTTASLSASVGETVTITCRASENIHNYLAWYQQKQGRSPQL LVYNAKTLGDGVPSRFSGSGSGTQYSLKINSLQPEDFGSYYCQHFW STPWTFGGGTKLEIK |
| 10B10 murine | Heavy chain variable | 17 | DVQLQESGPGLVTPSQSLSLTCSVTGYSITSGYSWNWIRQFPGNKL EWMGYIRFDGNNNYNPFLKNRISITRDTSENQFFLKLNSVTTEDTA TYYCARNYGTWGAMDFWGQGTSVTVSS |
| 10B10 murine | Light chain variable | 25 | DIVLTQSPSSLSASLGGKVTITCKTSQDINKYMAWYQHKPGKGPRL LIYYTSILQPGIPSRFSGSGSGTDYSFSINNLEPEDIATYYCQQYD NLNTFGGGTMLEIKR |
| 6F3 humanized | Heavy chain variable | 33 | QVQLVQSGAEVKKPGSSVKVSCKASGYTFTDYEMHWVRQAPGQGLE WIGVIDPETGGITYNQKFKGRATLTADKSTSTAYMELSSLRSEDTA VYYCTRRGARATVYNYVMDYWGQGTLVTVSS |
| 6F3 humanized | Light chain variable | 35 | DIQMTQSPSSLSASVGDRVTITCRASENIHNYLAWYQQKPGKAPKL LVYNAKTLGDGVPSRFSGSGSGTDYTLTISSLQPEDFATYYCQHFW STPWTFGGGTKVEIK |
| 10B10 humanized | Heavy chain variable | 37 | QVQLQESGPGLVKPSQTLSLTCAVSGYSITSGYSWNWIRQPPGKGL EWMGYIRFDGNNNYNPFLKNRITISRDTSKNQFSLKLSSVTAADTA VYYCARNYGTWGAMDFWGQGTLVTVSS |
| 10B10 humanized | Light chain variable | 39 | DIQLTQSPSSLSASVGDRVTITCKTSQDINKYMAWYQQKPGKAPKL LIYYTSILQPGVPSRFSGSGSGTDYTFTISSLQPEDIATYYCQQYD NLNTFGGGTKVEIK |
| 6F3 humanized | Full length heavy chain | 41 | QVQLVQSGAEVKKPGSSVKVSCKASGYTFTDYEMHWVRQAPGQGLE WIGVIDPETGGITYNQKFKGRATLTADKSTSTAYMELSSLRSEDTA VYYCTRRGARATVYNYVMDYWGQGTLVTVSSASTKGPSVFPLAPSS KSTSGGTAALGCLVKDYFPEPVTVSWNSGALTSGVHTFPAVLQSSG LYSLSSVVTVPSSSLGTQTYICNVNHKPSNTKVDKRVEPKSCDKTH TCPPCPAPELLGGPSVFLFPPKPKDTLMISRTPEVTCVVVDVSHED PEVKFNWYVDGVEVHNAKTKPREEQYNSTYRVVSVLTVLHQDWLNG KEYKCKVSNKALPAPIEKTISKAKGQPREPQVYTLPPSRDELTKNQ VSLTCLVKGFYPSDIAVEWESNGQPENNYKTTPPVLDSDGSFFLYS KLTVDKSRWQQGNVFSCSVMHEALHNHYTQKSLSLSPGK |
| 6F3 humanized | Full length light chain | 43 | DIQMTQSPSSLSASVGDRVTITCRASENIHNYLAWYQQKPGKAPKL LVYNAKTLGDGVPSRFSGSGSGTDYTLTISSLQPEDFATYYCQHFW STPWTFGGGTKVEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |
| 10B10 humanized | Full length heavy chain | 45 | QVQLQESGPGLVKPSQTLSLTCAVSGYSITSGYSWNWIRQPPGKGL EWMGYIRFDGNNNYNPFLKNRITISRDTSKNQFSLKLSSVTAADTA VYYCARNYGTWGAMDFWGQGTLVTVSSASTKGPSVFPLAPSSKSTS GGTAALGCLVKDYFPEPVTVSWNSGALTSGVHTFPAVLQSSGLYSL SSVVTVPSSSLGTQTYICNVNHKPSNTKVDKRVEPKSCDKTHTCPP CPAPELLGGPSVFLFPPKPKDTLMISRTPEVTCVVVDVSHEDPEVK FNWYVDGVEVHNAKTKPREEQYNSTYRVVSVLTVLHQDWLNGKEYK CKVSNKALPAPIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK |
| 10B10 humanized | Full length light chain | 47 | DIQLTQSPSSLSASVGDRVTITCKTSQDINKYMAWYQQKPGKAPKL LIYYTSILQPGVPSRFSGSGSGTDYTFTISSLQPEDIATYYCQQYD NLNTFGGGTKVEIKRTVAAPSVFIFPPSDEQLKSGTASVVCLLNNF YPREAKVQWKVDNALQSGNSQESVTEQDSKDSTYSLSSTLTLSKAD YEKHKVYACEVTHQGLSSPVTKSFNRGEC |

In certain embodiments, one or more CDR sequences provided herein can be modified or changed such that the resulting antibody is improved over the parent antibody in one or more properties (such as improved antigen-binding, improved glycosylation pattern, reduced risk of glycosylation on a CDR residue, reduced deamination on a CDR residue, increased pharmacokinetic half-life, pH sensitivity, and compatibility to conjugation), and is otherwise comparable to the parent antibody (i.e. antibody having otherwise the same set of CDR sequences except for the above-mentioned modification or change), or at least substantially retains the antigen-binding property of the parent antibody.

A skilled artisan will understand that the CDR sequences provided herein can be modified to contain one or more substitutions of amino acids, so as to provide for an improved biological activity such as improved binding affinity to human CTLA4. For example, a library of antibody variants (such as Fab or scFv variants) can be generated and expressed with phage display technology, and then screened for the binding affinity to human CTLA4. For another example, computer software can be used to virtually simulate the binding of the antibodies to human CTLA4, and identify the amino acid residues on the antibodies which form the binding interface. Such residues may be either avoided in the substitution so as to prevent reduction in binding affinity, or targeted for substitution to provide for a stronger binding. In certain embodiments, at least one (or all) of the substitution(s) in the CDR sequences is conservative substitution.

In certain embodiments, the antibodies and the antigen-binding fragments thereof comprise one or more CDR sequences having at least 80% (e.g. at least 85%, 88%, 90%, 91%, 92%, 93%, 94%, 95%, 96%, 97%, 98%, 99%) sequence identity to that (or those) listed in Tables 1 and 2, and in the meantime retain the binding affinity to human CTLA4 at a level similar to or even higher than its parental antibody having substantially the same sequence except that the corresponding CDR sequence is in 100% sequence identity to that (or those) listed in Tables 1 and 2.

In certain embodiments, the anti-CTLA4 antibodies and the antigen-binding fragments thereof are humanized. The humanized antibodies do not have the issues of immunogenicity in human and/or reduced binding affinity as often observed with humanized antibodies. Theses humanized antibodies retain the binding affinity to human CTLA4, preferably at a level similar to one of the exemplary antibodies: 6F3 and 10B10.

Also contemplated herein are antibodies and the antigen-binding fragments that compete for the same epitope with the anti-CTLA4 antibodies and the antigen-binding fragments thereof provided herein. In certain embodiments, the antibodies block binding of 6F3, 10B10, 6F3 humanized or 10B10 humanized to human or monkey CTLA4, for example, at an IC50 value (i.e. 50% inhibition concentration) of below $10^{-6}$ M, below $10^{-7}$ M, below $10^{-7.5}$ M, below $10^{-8}$ M, below $10^{-8.5}$ M, below $10^{-9}$ M, or below $10^{-10}$ M. The $IC_{50}$ values are determined based on a competition assay such as ELISA assays, radioligand competition binding assays, and FACS analysis.

In some embodiments, the anti-CTLA4 antibodies and the antigen-binding fragments thereof provided herein are capable of specifically binding to human CTLA4 with a binding affinity (Kd) of $^{-6}$ M (e.g., $\leq 5 \times 10^{-7}$ M, $\leq 2 \times 10^{-7}$ M, $\leq 10^{-7}$ M, $\leq 5 \times 10^{-8}$ M, $\leq 2 \times 10^{-8}$ M, $\leq 10^{-8}$ M, $\leq 5^{-9}$ M, $\leq 2 \times 10^{-9}$ M, $\leq 10^{-9}$ M, $^{-10}$ M) as measured by plasmon resonance binding assay or ELISA. The binding affinity can be represented by $K_D$ value, which is calculated as the ratio of dissociation rate to association rate ($k_{off}/k_{on}$) when the binding between the antigen and the antigen-binding molecule reaches equilibrium. The antigen-binding affinity (e.g. $K_D$) can be appropriately determined using suitable methods known in the art, including, for example, plasmon resonance binding assay using instruments such as Biacore (see, for example, Murphy, M. et al, Current protocols in protein science, Chapter 19, unit 19.14, 2006).

In certain embodiments, the antibodies and the fragments thereof provided herein binds to human CTLA4 with an $EC_{50}$ (i.e. 50% binding concentration) of 0.05 nM-1 nM (e.g. 0.1 nM-0.9 nM, 0.1 nM-0.8 nM, 0.1 nM-0.7 nM, 0.1 nM-0.6 nM, 0.1 nM-0.5 nM, 0.1 nM-0.4 nM, 0.1 nM-0.3 nM, or 0.1 nM-0.2 nM). Binding of the antibodies to human CTLA4 can be measured by methods known in the art, for example, sandwich assay such as ELISA, Western Blot, other binding assay. In an illustrative example, the test antibody (i.e. first antibody) is allowed to bind to immobilized human CTLA4, after washing away the unbound antibody, a labeled secondary antibody is introduced which can bind to and thus allow detection of the bound first antibody. The detection can be conducted with a microplate reader when immobilized CTLA4 is used.

In certain embodiments, the antibodies and the fragments thereof provided herein inhibit the binding of human CTLA4 to human B7.1 or B7.2 at an $IC_{50}$ of 3 nM-10 nM (e.g. 3.5 nM-9.5 nM, 3.5 nM-8.5 nM, or 5 nM-8.5 nM), as measured in a competition assay.

In some embodiments, the anti-CTLA4 antibodies and the antigen-binding fragments thereof further comprise an immunoglobulin constant region. In some embodiments, an immunoglobulin constant region comprises a heavy chain and/or a light chain constant region. The heavy chain constant region comprises CH1, CH1-CH2, or CH1-CH3 regions. In some embodiments, the constant region may further comprise one or more modifications to confer desirable properties. For example, the constant region may be modified to reduce or deplete one or more effector functions, to improve FcRn receptor binding, or to introduce one or more cysteine residues. In some embodiments, the anti-CTLA4 antibodies and the antigen-binding fragments thereof have a constant region of IgG4 isotype, which has reduced or depleted effector function. Various assays are known to evaluate ADCC or CDC activities, for example, Fc receptor binding assay, C1q binding assay, and cell lysis assay, and can be readily selected by people in the art.

In certain embodiments, the antibodies and antigen-binding fragments thereof can be used as the base of antibody-drug conjugates, bispecific or multivalent antibodies.

The anti-CTLA4 antibodies or antigen-binding fragments thereof provided herein can be a monoclonal antibody, polyclonal antibody, humanized antibody, chimeric antibody, recombinant antibody, bispecific antibody, labeled antibody, bivalent antibody, or anti-idiotypic antibody. A recombinant antibody is an antibody prepared in vitro using recombinant methods rather than in animals. A bispecific or bivalent antibody is an artificial antibody having fragments of two different monoclonal antibodies and can bind two different antigens. An antibody or antigen-binding fragment thereof that is "bivalent" comprises two antigen-binding sites. The two antigen binding sites may bind to the same antigen, or they may each bind to a different antigen, in which case the antibody or antigen-binding fragment is characterized as "bispecific."

In some embodiments, the anti-CTLA4 antibodies and the antigen-binding fragments thereof is a camelized single domain antibody, a diabody, a scFv, an scFv dimer, a BsFv, a dsFv, a (dsFv)2, a dsFv-dsFv', an Fv fragment, a Fab, a Fab', a F(ab')2, a ds diabody, a nanobody, a domain antibody, or a bivalent domain antibody.

In some embodiments, the anti-CTLA4 antibodies and the antigen-binding fragments thereof further comprise a conjugate. It is contemplated that a variety of conjugates may be linked to the antibodies or antigen-binding fragments provided herein (see, for example, "Conjugate Vaccines", Contributions to Microbiology and Immunology, J. M. Cruse and R. E. Lewis, Jr. (eds.), Carger Press, New York, (1989)). These conjugates may be linked to the antibodies or antigen-binding fragments by covalent binding, affinity binding, intercalation, coordinate binding, complexation, association, blending, or addition, among other methods. In certain embodiments, the antibodies and antigen-binding fragments disclosed herein may be engineered to contain specific sites outside the epitope binding portion that may be utilized for binding to one or more conjugates. For example, such a site may include one or more reactive amino acid residues, such as for example cysteine or histidine residues, to facilitate covalent linkage to a conjugate. In certain embodiments, the antibodies may be linked to a conjugate indirectly, or through another conjugate. For example, the antibody or antigen-binding fragments may be conjugated to biotin, then indirectly conjugated to a second conjugate that is conjugated to avidin. The conjugate can be a detectable label, a pharmacokinetic modifying moiety, a purification moiety, or a cytotoxic moiety. Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or 3-D-galactosidase), radioisotopes (e.g. $^{123}$I, $^{124}$I, $^{125}$I, $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, and $^{32}$P, other lanthanides, luminescent labels), chromophoric moiety, digoxigenin, biotin/avidin, a DNA molecule or gold for detection. In certain embodiments, the conjugate can be a pharmacokinetic modifying moiety such as PEG which helps increase half-life of the antibody. Other suitable polymers include, such as, carboxymethylcellulose, dextran, polyvinyl alcohol, polyvinyl pyrrolidone, copolymers of ethylene glycol/propylene glycol, and the like. In certain embodiments, the conjugate can be a purification moiety such as a magnetic bead. A "cytotoxic moiety" can be any agent that is detrimental to cells or that can damage or kill cells. Examples of cytotoxic moiety include, without limitation, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Polynucleotides and Recombinant Methods

The present disclosure provides isolated polynucleotides that encode the anti-CTLA4 antibodies and the antigen-binding fragments thereof. In certain embodiments, the isolated polynucleotides comprise one or more nucleotide sequences as shown in Table 1 and 2, which encodes the CDR sequences provided in Table 1.

In some embodiments, the isolated polynucleotides encodes a heavy chain variable region and comprise a sequence selected from the group consisting of: SEQ ID NO: 2, SEQ ID NO: 18, SEQ ID NO: 34, SEQ ID NO: 38, and a homologous sequence thereof having at least 80% (e.g. at least 85%, 88%, 90%, 91%, 92%, 93%, 94%, 95%, 96%, 97%, 98%, 99%) sequence identity. In some embodiments, the isolated polynucleotides encodes a light chain variable region and comprise a sequence selected from the group consisting of: SEQ ID NO: 10, SEQ ID NO: 26, SEQ ID NO: 36, SEQ ID NO: 40 and a homologous sequence thereof having at least 80% (e.g. at least 85%, 88%, 90%, 91%, 92%, 93%, 94%, 95%, 96%, 97%, 98%, 99%) sequence identity. In certain embodiments, the percentage identity is due to genetic code degeneracy, while the encoded protein sequence remains unchanged.

The isolated polynucleotide that encodes the anti-CTLA4 antibodies and the antigen-binding fragments thereof (e.g. including the sequences in Table 1) can be inserted into a vector for further cloning (amplification of the DNA) or for expression, using recombinant techniques known in the art. In another embodiment, the antibody may be produced by homologous recombination known in the art. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence.

In some embodiments, the vector system includes mammalian, bacterial, yeast systems, etc, and comprises plasmids such as, but not limited to, pALTER, pBAD, pcDNA, pCal, pL, pET, pGEMEX, pGEX, pCI, pCMV, pEGFP, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS420, pLexA, pACT2.2 etc, and other laboratorial and commercially available vectors. Suitable vectors may include, plasmid, or viral vectors (e.g., replication defective retroviruses, adenoviruses and adeno-associated viruses).

Vectors comprising the polynucleotide sequence encoding the antibody or antigen-binding fragment can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

In addition to prokaryotes, eukaryotic microbes such as filamentous fungi or yeast are suitable cloning or expression hosts for anti-CTLA4 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2). In some preferable embodiments, the host cell is 293F cell.

Host cells are transformed with the above-described expression or cloning vectors for anti-CTLA4 antibody production and cultured in conventional nutrient media modified as appropriate for inducing promoters, selecting transformants, or amplifying the genes encoding the desired sequences.

The host cells used to produce the antibodies or antigen-binding fragments provided herein may be cultured in a variety of media. Commercially available media such as Ham's F10 (Sigma), Minimal Essential Medium (MEM) (Sigma), RPMI-1640 (Sigma), and Dulbecco's Modified Eagle's Medium (DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human .gamma.1, .gamma.2, or .gamma.4 heavy chains (Lindmark et al., J. Immunol. Meth. 62:1-13 (1983)). Protein G is recommended for all mouse isotypes and for human .gamma.3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Kits

The present disclosure provides kits comprising the anti-CTLA4 antibodies used to bind CTLA4 in a biological sample. The biological sample can comprise plasma. In some embodiments, the kit comprises an anti-CTLA4 antibody or the antigen-binding fragment thereof which is conjugated with a detectable label. In certain other embodiments, the kit comprises an unlabeled anti-CTLA4 antibody or antigen-binding fragment, and further comprises a secondary labeled antibody which is capable of binding to the unlabeled anti-CTLA4 antibody. The kit may further comprise an instruction of use, and a package that separates each of the components in the kit.

In some embodiments, the kits are useful for treating preventing, or delaying diseases or conditions mediated by CTLA4. In certain embodiments, the anti-CTLA4 antibody or the antigen-binding fragment thereof are associated with a substrate or a device useful in a sandwich assay such as ELISA, or in an immunographic assay. Useful substrate or device can be, for example, microtiter plate and test strip.

Pharmaceutical Composition and Method of Treatment

The present disclosure further provides pharmaceutical compositions comprising the anti-CTLA4 antibodies or the antigen-binding fragments thereof and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylceluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-CTLA4 antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Therapeutic methods are also provided, comprising: administering a therapeutically effective amount of the antibody or antigen-binding fragment as provided herein to a subject in need thereof, thereby treating or preventing a condition or a disorder associated with related to CTLA4. In another aspect, methods are provided to treat a condition in a subject that would benefit from upregulation of immune response, comprising administering a therapeutically effective amount of the antibody or antigen-binding fragment as provided herein to a subject in need thereof.

The therapeutically effective amount of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of tumor development. Dosages may be proportionally reduced or increased by one of ordinary skill in the art (e.g., physician or veterinarian) as indicated by these and other circumstances or requirements.

In certain embodiments, an antibody or antigen-binding fragment as provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 3 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the antibody or antigen-binding fragment is administered at a dosage of about 50 mg/kg or less, and in certain of these embodiments the dosage is 10 mg/kg or less, 5 mg/kg or less, 3 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

Conditions and disorders associated with CTLA4 can be immune related disease or disorder. In certain embodiments, the CTLA4 associated conditions and disorders include tumors and cancers, for example, non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies, such as classical Hodgkin lymphoma (CHL), primary mediastinal large B-cell lymphoma, T-cell/histiocyte-rich B-cell lymphoma, EBV-positive and -negative PTLD, and EBV-associated diffuse large B-cell lymphoma (DLBCL), plasmablastic lymphoma, extranodal NK/T-cell lymphoma, nasopharyngeal carcinoma, and HHV8-associated primary effusion lymphoma, Hodgkin's lymphoma, neoplasm of the central nervous system (CNS), such as primary CNS lymphoma, spinal axis tumor, brain stem glioma. In certain embodiments, the tumors and cancers are metastatic, especially metastatic tumors expressing PD-L1. In certain embodiments, the PD-1 associated conditions and disorders include autoimmune diseases, such as systemic lupus erythematosus (SLE), psoriasis, systemic scleroderma, autoimmune diabetes and the like. In certain embodiments, the PD-1 associated conditions and disorders include infectious disease such as chronic viral infection, for example, viral infection of hepatitis B, hepatitis C, herpes virus, Epstein-Barr virus, HIV, cytomegalovirus, herpes simplex virus type I, herpes simplex virus type 2, human papilloma virus, adenovirus, Kaposi West sarcoma associated herpes virus epidemics, thin ring virus (Torquetenovirus), JC virus or BK virus.

Methods of Use

The present disclosure further provides methods of using the anti-CTLA4 antibodies or the antigen-binding fragments thereof.

In some embodiments, the present disclosure provides methods of treating a condition mediated by CTLA4 in an individual, comprising administering a therapeutically effective amount of the anti-CTLA4 antibody or antigen-binding fragment thereof. In certain embodiments, the individual has been identified as having a disorder or condition likely to respond to a CTLA4 antagonist. In certain embodiments, the disorder or condition includes tumors or cancers.

In certain of these embodiments, an antibody or antigen-binding fragment as disclosed herein that is administered in combination with one or more above additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1

Mouse Immunization and Production of Mouse Antibodies Against Human CTLA4

To generate antibodies against the human CTLA4, cDNAs encoding the open reading frame of the extracellular domain of CTLA4 fused with a histidine tag (hCTLA4-His, SEQ ID NO:49), mouse Fc (hCTLA4-mFc, SEQ ID NO:51), and human Fc tag (hCTLA4-hFc, SEQ ID NO:53) were obtained by PCR and subcloned into expression vector pcDNA3.1 (Invitrogen Cat No: V-790), respectively. After transient expression in freestyle 293 cells, hCTLA4-HisTag was purified with NTA column (GE healthcare), and hCTLA4-mFc and hCTLA4-hFc were purified with Protein G column (GE healthcare).

To immunize mice necessary for generating hybridoma cell lines, 100 μg of human CTLA4-mFc fusion protein and 100 μl complete Freund's adjuvant were mixed, and the mixture was administered via an subcutaneous injection to each of five 6 to 7-week-old BALB/c mice. After two weeks, the antigen (half the previously injected amount) was mixed with an incomplete Freund's adjuvant using the same method as described above, and the mixture was administered to each mouse via subcutaneous injection. After one week, final boosting was performed. Three days later, blood was collected from the tail of each mouse to obtain serum. The serum was then diluted at 1/1000 with PBS, and an ELISA was performed to analyze whether the titer of the antibody recognizing human CTLA4-mFc increased. Afterwards, mice in which a sufficient amount of the antibody was obtained were selected, and a cell fusion process was performed on the selected mice.

Three days before a cell fusion experiment, 50 μg human CTLA4-mFc fusion protein was administered via an intraperitoneal injection to each mouse. Each immunized mouse was anesthetized, and its spleen located on the left side of the body was then extracted and ground with a mesh to isolate cells, which were mixed with a culture medium (RPMI1640) to prepare a spleen cell suspension. The suspension was centrifuged to collect a cell layer. The obtained $1\times10^8$ of spleen cells were mixed with $1.5\times10^7$ of myeloma cells (Sp2/0), and the mixture was centrifuged to precipitate the cells. The precipitate was slowly dispersed and treated with PEG Hybri-Max (Sigma Inc., Cat No: 7181). The mixed cells were distributed into 96-well plates at 0.1 ml per well and incubated at 37° C., 5% $CO_2$ incubator. On day 1, the cells were fed by the addition of an additional 0.1 ml media containing serum and HAT plus 2×methotrexate for each well. On day 3 and day 7, 0.1 ml of medium from each well was replaced with 0.1 ml of fresh HT medium. The screening typically occurred between days 9-14.

Example 2

Selection of the Hybridoma Cells that Produce Monoclonal Antibodies Against Human CTLA4 Based on ELISA and FACS Analyses.

ELISA binding analysis was conducted using human CTLA4-hFc. 96-well plates (Costar, Cat No: 9018) were coated with 100 μl of 2 μg/ml CTLA4-hFc (CrownBio) in coating buffer (PBS, Hyclone, Cat No: SH30256.01B) overnight at 4° C. The wells were aspirated and non-specific binding sites were blocked by adding 200 μl of blocking buffer with 1% (w/v) of bovine serum albumin (BSA, Roche, Cat No: 738328) and incubating for 1 hour at 37° C. After the plates are washed three times with wash buffer (PBS with 0.05% (v/v) TWEEN-20™ (Sigma, Cat No: P1379)), 100 μl/well of a suitable dilutions of hybridoma supernatant in blocking buffer were added and incubated at room temperature for 1 hour. The plates were washed and incubated with 100 μl/well of Goat anti-Mouse IgG (H+L) (Thermo, Cat No: 31432) in blocking buffer for 60 min. After the plates were washed, 100 μl/well of substrate solution TMB (eBioscience, Cat No: 00-4201-56) was added and the plates were incubated for 2 min at room temperature. 100 μl/well of stop solution (2N $H_2SO_4$) was added to stop the reaction. The colorimetric signals were developed and read at 450 nm using a Auto Plate SpectraMax Plus (Supplier: Molecular Devices; Model: MNR0643; Software: SoftMax Pro v5.4). Through this method, hybridoma cell lines that produce antibodies highly specifically binding to the human CTLA4 protein were repeatedly selected.

ELISA based ligand blockage analysis was conducted via blocking biotinylated human CD80-mFc from binding to human CTLA4-mFc. CTLA4-mFc antigen (CrownBio) was suspended in PBS (Hyclone, Cat No: SH30256.01B) buffer (2 μg/ml, 100 μl/well) and coated on the 96 well plate (Costar, Cat No: 9018) 4° C. overnight. Plates were washed 3 times using washing buffer: PBS+0.05% Tween 20 (Sigma, Cat No: P1379). 200 μl of blocking buffer (PBS+1% BSA (Roche, Cat No: 738328)) was added to each well, incubated at 37° C. for 1 hour, and washed 3 times. Various concentrations (suitable dilutions of hybridoma supernatant in PBS) of the anti-CTLA4 antibodies were added to the wells (100 μl/well) and incubated at 37° C. for 1 hour. Ligand was added (0.1 μg/ml CD80-mFc-biotin, 100 μl/well), incubated at 37° C. for 2 hours, and washed 3 times. Secondary antibody (Avidin HRP, eBioscience Cat No: E07418-1632, 1:500, 100 μl/well) was added, incubated at 37° C. for 0.5 hour, and washed 3 times. TMB (Sigma, Cat No: T0440, 100 μl/well) was added, and incubated for 3 min at room temperature. To stop the reaction, 2N $H_2SO_4$ (100 μl/well), was added. The colorimetric signals were developed and read at 450 nm using an Auto Plate SpectraMax Plus (Supplier: Molecular Devices; Model: MNR0643; Software: SoftMax Pro v5.4).

Cell binding analysis of antibodies was performed using hCTLA4-293T cell line. $2\times10^5$ 293T-CTLA4 cells were used for each reaction by putting them into each well of 96-well culture plates. The cells were incubated with the indicated antibody (20 μg/ml with the dilution of 1/5) at 4° C. for 1 hour. Cells were washed three times with FACS buffer. A secondary antibody (PE Goat anti-mouse: 1:200; PE mouse anti-human: 1:10) was added to the cells at 100 μl/well, and incubated at 4° C. for 40 min. Cells were washed three times with FACS buffer and analyzed by FACS Array.

FACS based ligand blockage analysis was conducted to determine the anti-CTLA4 hybridoma antibodies in the blockage of biotinylated human CD80 binding to hCTLA4-293T cells. CTLA4 expressing 293T cells were suspended in FACS buffer (PBS with 3% fetal calf serum). Various concentrations of the testing hybridoma antibodies were added to the cell suspension and incubated at 4° C. for 60 minutes in 96 well plates. Biotin-labeled CD80 protein was added into the wells and incubated at 4° C. for 60 minutes. Plates were washed 3 times, and mouse anti-biotin PE antibody (Biolgend, Cat No 409004) was added. Flow cytometric analyses were performed using a FACS Array.

Figure 2:
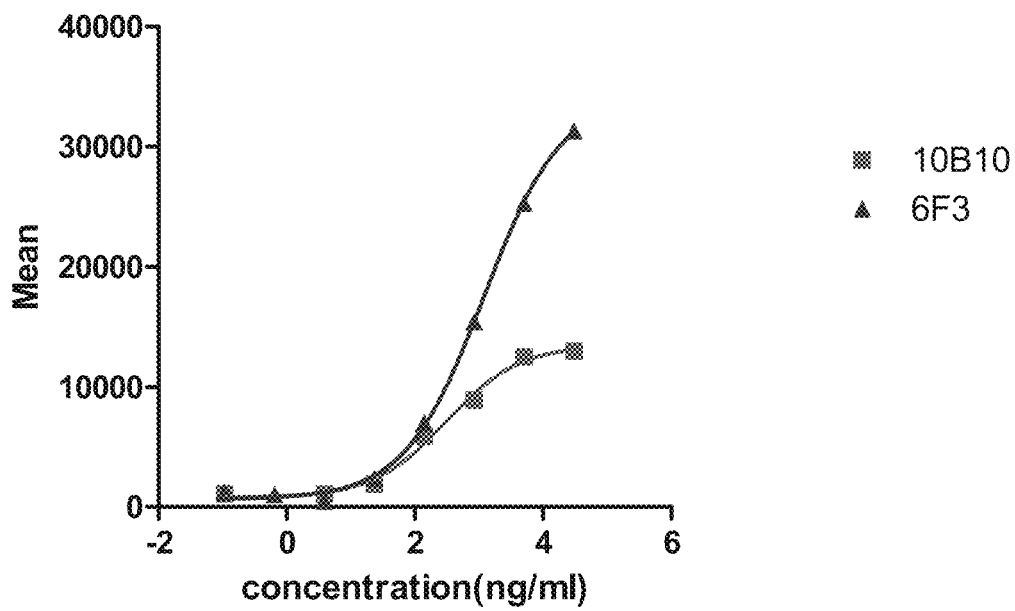
FIG. 2 shows the binding EC50 of murine antibody 6F3 and 10B10 as measured by FACS. The top panel of the figure shows the mean fluorescence intensity (MFI) over a range of concentrations of murine antibodies, and the bottom panel of the figure shows the calculated EC50 of each of the test antibodies.
Figure 3:
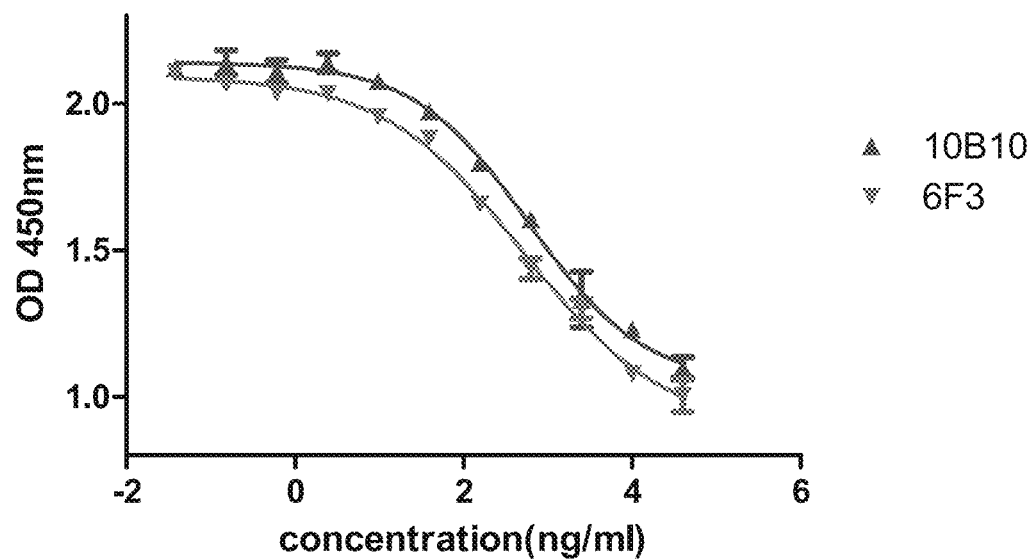
FIG. 3 shows blockage of CTLA4 ligand CD80 binding to CTLA4 by murine anti-CTLA4 antibody 6F3 and 10B10 as measured by ELISA. The top panel of the figure shows the absorbance over a range of antibody concentrations. The blockage IC50 for the anti-CTLA4 antibodies is shown in the bottom panel of FIG. 3.
Figure 4:
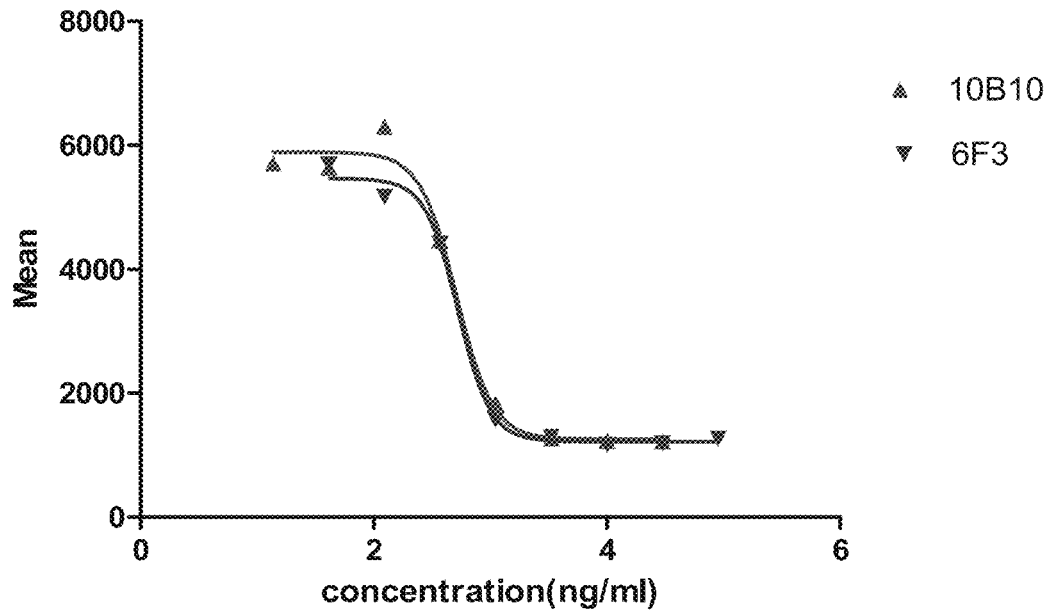
FIG. 4 shows blockage of CTLA4 ligand CD80 binding to CTLA4 by murine anti-CTLA4 antibody 6F3 and 10B10 as measured by FACS. The top panel of the figure shows the MFI over a range of antibody concentrations. The blockage IC50 for the anti-CTLA4 antibodies is shown in the bottom panel of FIG. 4.

The results of the study are depicted in FIG. 1-4. The anti-CTLA4 monoclonal antibodies can bind CTLA4 on solid phase (FIG. 1) and cell surface (FIG. 2). The antibodies can also block binding of CD80 to CTLA4 on 96-well plate (FIG. 3) or 293T cells transfected with human CTLA4 (FIG. 4). These data demonstrated that the anti-CTLA4 antibodies can binding CTLA4 and block its binding with ligand CD80.

Example 3

Subcloning to Obtain Monoclonal Antibody Clones and Purification of Anti-hCTLA4 Antibodies Subcloning is based on the procedure of limited dilution, and is designed to obtain individual hybridoma clones producing monoclonal antibodies. Each of the hybridomas was subjected to multiple rounds (4 rounds) of limiting dilution. For each round of subcloning, the clones were tested by ELISA and FACS based blockage analyses.

Antibody purification was conducted for a total of twenty anti-hCTLA4 hybridoma antibodies. The hybridoma cells were cultured in Dulbecco's Modified Eagle's medium (GIBCO; Invitrogen Corporation, Carlsbad, Calif.) containing 10% fetal calf serum, 1% penicillin/streptomycin, 2% L-glutamine, and 1% adjusted $NaHCO_3$ solution. The selected hybridoma cells were then adapted in serum free culture medium and the antibody was purified from the supernatant using Protein-G column (GE healthcare). After washing with PBS, bound antibodies were eluted using 0.1 M Glycine pH3.0, followed by pH neutralization using 2.0 M Tris. Ultra-15 centrifugal concentrators (Amicon) were used for buffer exchanging and antibody concentrating.

Example 4

Characterization of the Purified Murine Anti-hCTLA4 Antibodies in Binding and Ligand Blockage Activities Based on ELISA and FACS Analyses The purified hybridoma antibodies were characterized further based on ELISA and FACS analyses. The methods applied were similar to those described above in Example 2 except that in these cases, purified antibodies were used to measure EC50 and IC50. Tables 5-8 show the results of antibody 6F3 and 10B10.

TABLE 5

ELISA based binding EC50 of murine anti-CTLA4 antibodies

| ng/ml | 6F3 | 10B10 |
| --- | --- | --- |
| EC50 | 24.97 | 12.68 |

TABLE 6

ELISA based blockage IC50 of murine anti-CTLA4 antibodies

| ng/ml | 6F3 | 10B10 |
| --- | --- | --- |
| IC50 | 526.3 | 594.0 |

TABLE 7

FACS based binding EC50 of murine anti-CTLA4 antibodies

| ng/ml | 6F3 | 10B10 |
| --- | --- | --- |
| EC50 | 1179 | 305.5 |

TABLE 8

FACS based blockage IC50 of murine anti-CTLA4 antibodies

| ng/ml | 6F3 | 10B10 |
| --- | --- | --- |
| IC50 | 525.7 | 511.3 |

Example 5

Biacore Analysis of the Murine Anti-CTLA4 Antibodies

To further characterize the binding characteristics of the antibodies, the hybridoma antibodies were profiled using Biacore (Biacore 3000, GE) to elucidate binding kinetics and calculate equilibrium binding constants. This assay was performed by capture method, using the mouse antibody capture kit (BR-1008-38, GE). After diluting anti-mouse Fc mab to 25 µg/ml in pH 5.0 immobilization buffer, immobilization was conducted with the parameters shown in Table 9 at a flow rate of 5 µl/min. The kinetic runs were done by 1) injecting ligand for typical 0.5-1 min at flow rate of 10 µl/min.; 2) injecting analytes of choice for typical 3 min followed by dissociation in running buffer (1×PBS-P20) for typical 5-10 min at flow rate of 30 µl/min.; and 3) injecting regeneration solution 10 mM Glycine pH 1.7 for typical 1-2 min at flow rate of 10 µl/min.

TABLE 9

Biacore parameters.

| Event | Injection | Conditions |
| --- | --- | --- |
| Activation | EDC/NHS (1:1 Mix) | 7 minutes |
| Immobilization | Diluted Anti-human Fc mAb | 4 minutes to achieve ~7000 RU Immobilization level |
| Deactivation | Ethanolamine-HCl | 7 minutes |

The results of the study are shown in Table 10. Both 6F3 and 10B10 have a high binding affinity with CTLA4.

TABLE 10

Binding kinetics of anti-CTLA4 hybridoma antibodies with CTLA4.

| | ka (1/Ms) | kd (1/s) | Kd (M) | Chi2 |
| --- | --- | --- | --- | --- |
| 10B10 | 6.93E+05 | 1.52E−04 | 2.19E−10 | 0.39 |
| 6F3 | 5.98E+05 | 2.44E−04 | 4.09E−10 | 0.24 |

Example 6

Cross-Reactivity Among Species and Among Similar Molecules

To assess the species cross-reactivity of the antibodies, the mouse and cynomolgus macaque CTLA4 were cloned by RT-PCR, expressed in freestyle 293 cells and purified. The antibodies were tested for binding to the cynomolgus CTLA4 using protein based ELISA. The results of the study showed that the antibodies bind with equal affinity to human and cynomolgus CTLA4 and block binding of CD80 to cynomolgous CTLA4 with similar efficacy as compared to human CTLA4. None of the antibodies selected bound mouse CTLA4 with detectable affinity in any of the assays used. None cross reacts with human ICOS and CD28.

Example 7

Effect of the Anti-CTLA4 Hybridoma Antibodies on Cytokine Production by PBMC

Figure 9:
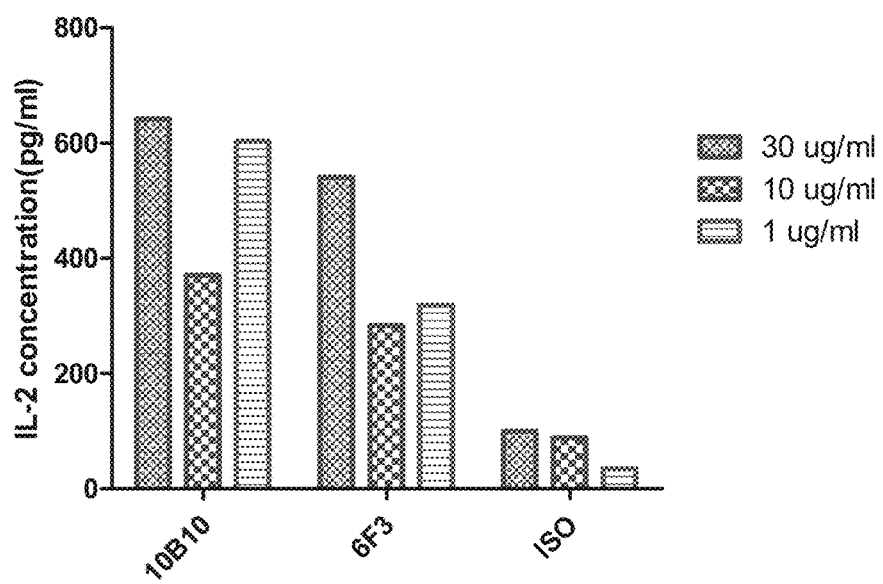
FIG. 9 is a graph showing IL-2 (pg/mL) production by PBMC in response to different concentrations of murine anti-CTLA4 antibodies. The murine anti-CTLA4 antibodies tested were, from left to right, 10B10, 6F3, mIgG1 isotype control. As shown on the x-axis, each antibody was tested at 30 µg/mL, 10 µg/mL, 1 µg/mL.
Figure 10:
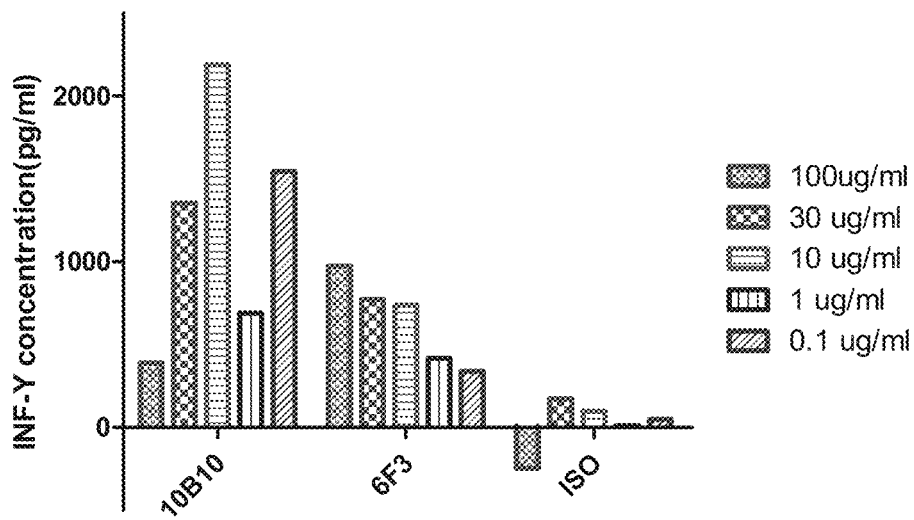
FIG. 10 is a graph showing IFN-γ (pg/mL) production by PBMC in response to different concentrations of murine anti-CTLA4 antibodies. The murine anti-CTLA4 antibodies tested were, from left to right, 10B10, 6F3, mIgG1 isotype control. As shown on the x-axis, each antibody was tested at 30 µg/mL, 10 µg/mL, 1 µg/mL.

The activity of the CTLA4 hybridoma antibody was evaluated by its effect on blocking the CTLA4 signaling pathway in lymphocyte effector cells. Freshly isolated human PBMCs were prepared by using Histopaque (Sigma, Cat No: 1077-1), and stimulated with 5 ng/ml staphylcoccus enterotoxin B (SEB) (Sigma) in RPMI 1640 supplemented with 10% FBS at a concentration of $2\times10^6$ cells/ml. 100 µl PBMCs were then added to each of the wells ($2\times10^5$ cells per well) on 96-well plate in the presence or absence of CTLA4 antibody. A series of concentrations (30 µg/ml, 10 µg/ml, 1 µg/ml) of the antibody were tested. After incubated at 37° C. for 72 or 96 hours, the 96-well plate was centrifuged and the supernatants were collected to measure IL-2 and IFN-γ production using ELISA kit (R&D Systems, Cat No: DY285). Isotype control antibody was used as a negative control. The results of the study are provided in FIG. 9 (IL-2 secretion) and FIG. 10 (IFN-γ secretion), demonstrating that the anti-CTLA4 monoclonal antibody 6F3 and 10B10 can promote IFN-γ and IL-2 secretion by PBMC. In contrast, cultures containing the isotype control antibody did not show any increase in IFN-γ or IL-2 secretion.

Example 8

Anti-CTLA4 Antibody cDNA Sequences Cloning and Humanization

Cloning of Immunoglobulin cDNAs

Total RNA isolated from the hybridoma cell line producing hCTLA4 antibody by RNeasy Mini Kit (Qiagen, Cat No: 74104) was used as the template to synthesize first-strand cDNA with SuperScript® II Reverse Transcriptase (Life Technology, Cat No: 18064-14) according to the manufacturer's instructions. The cDNA product was then subjected to PCR in a 50 µl volume reaction mixture using degenerate mouse IgG primers (Kettleborough et al, (1993) Eur J Immunology 23: 206-211; Strebe et al, (2010) Antibody Engineering 1:3-14). The reaction was carried out in a S1000™ Thermal Cycler (Bio-Rad, Cat No: 184-2000) with 30 cycles of: 94° C., 1.5 minutes for denaturation; 50° C., 1 minutes for annealing; and 72° C., 1 minute for synthesis. At the end of the 30th cycle, the reaction mixture was incubated another 7 minutes at 72° C. for extension.

The PCR mixture was subjected to electrophoresis in a 1% agarose/Tris-Borate gel containing 0.5 µg/ml ethidium bromide. DNA fragments having the expected sizes (approximately 400 bp for the heavy chain and the light chain) were excised from the gel and purified. 3 µl of purified PCR product was cloned into the pMD-18T vector (Takara, Cat No: D101A) and transformed into One Shot® TOP10 Chemically Competent *E. coli* (Invitrogen, Cat No: C4040-03). Clones were screened by colony PCR using universal M13 forward and reverse primers, and 10 positive clones from each reaction were chosen for DNA sequencing in both directions using M13 forward and M13 reverse primers.

The variable region sequences of antibodies 6F3 (SEQ ID NOs: 1 and 9), 10B10 (SEQ ID NOs: 17 and 25) were amplified from the corresponding hybridoma clones. These antibodies showed desired functions, such as blocking CTLA4 binding to CD80 and enhanced T cell activation and cytokine release.

Antibody Humanization Design

6F3 and 10B10 antibody were humanized using a CDR grafting approach (U.S. Pat. No. 5,225,539, incorporated herein by reference in its entirety). The light chain and heavy chain variable chain sequences of the murine antibody 6F3 and 10B10 were compared to those available in the Research Collaboratory for Structural Bioinformatics (RCSB) protein databank by searching the NCBI database. The model of 6F3 and 10B10 were generated respectively based on the VH and VL structure with the highest sequence homology.

The template human antibodies to be grafted with the complementary determining regions (CDRs) in the VH and VL of mouse 6F3 and 10B10 antibody were selected from human antibody germlines which have an amino acid sequence with high homology with the mouse 6F3 and 10B10 antibody by searching the IMGT/Domain Gap Align 3D structure database, http://www.imgt.org/3Dstructure-DB/cgi/DomainGapAlign.cgi. For 6F3, the template human VH selected was a combination of IGHV1-46*01 and IGHJ4*01, and template human VL selected was a combination of IGKV1-NL1*01 and IGKJ4*01. For 10B10, the template human VH selected was a combination of IGHV4-30-4*07 and IGHJ1*01, and template human VL selected was a combination of IGKV1-33*01 and IGKJ4*01.

CDR amino acid sequences of the aforementioned template human antibodies were substituted by those of CDRs of murine 6F3 and 10B10 antibody, respectively. In addition, the frameworks of the above-mentioned template human antibody VH and VL were grafted with the necessary amino acid sequences from VH and VL of mouse 6F3 and 10B10 antibody to give a functional humanized antibody. As for VH and VL of 6F3 and 10B10, several sites of framework amino acid of the aforementioned template human antibody were back mutated to the corresponding amino acid sequences in mouse 6F3 and 10B10 antibody. For the humanization of 6F3 antibody light chain variable region, the amino acid at position 48 was mutated from Leu (L) to Val (V); and for the 6F3 antibody heavy chain variable region humanization, the amino acid at position 48 was mutated from Met (M) to Ile (I), the amino acid at position 67 was mutated from Val (V) to Ala (A), the amino acid at position 69 was mutated from Met (M) to Leu (L), the amino acid at position 71 was mutated from Arg (R) to Ala (A), the amino acid at position 73 was mutated from Thr (T) to Lys (K), the amino acid at position 78 was mutated from Val (V) to Ala (A), and the amino acid at position 93 was mutated from Ala (A) to Thr (T). For the light chain variable region of humanized 10B10 antibody, the amino acid at position 4 was mutated from Met (M) to Leu (L), and the amino acid at position 71 was mutated from Phe (F) to Tyr (Y); and for the heavy chain variable region of humanized 10B10 antibody, the amino acid at position 27 was mutated from Gly (G) to Tyr (Y), the amino acid at position 30 was mutated from Ser (S) to Thr (T), the amino acid at position 48 was mutated from Ile (I) to Met (M), the amino acid at position 67 was mutated from Val (V) to Ile (I), and the amino acid at position 71 was mutated from Val (V) to Arg (R).

The amino acid sequences of the heavy and light chain variable region of humanized 6F3 antibody were designated SEQ ID NOs: 33 and 35, respectively. The DNA sequences encoding the heavy and light chain variable region were designed SEQ ID NOs: 34 and 36, respectively. The amino acid sequences of the variable light and variable heavy chains of humanized 10B10 antibody were designated SEQ ID NOs: 37 and 39, respectively. The base sequences of DNAs encoding the amino acid sequences were designed SEQ ID NO: 38 and 40, respectively.

IgG1 isotype of the humanized 6F3 or 10B10 antibody was produced (h6F3-IgG1 and h10B10-IgG1). The full length heavy and light chain amino acid sequences for h6F3-IgG1 (SEQ ID NOs: 41 and 43), h10B10-IgG1 (SEQ ID NOs: 45 and 47) are provided above in Table 4.

Construction and Expression of Humanized 6F3 and 10B10 Antibodies

DNA encoding humanized 6F3 and 10B10 antibody light chain and heavy chain was synthesized and cloned to the expression vector pcDNA3.1 (Invitrogen, Cat No: V-790). Freestyle 293 cells (200 mL at $10^6$/mL) were transfected with 100 μg of each of the humanized heavy and light chain expression plasmids and cultured for 6 days. The humanized antibody in the supernatant was then purified with Protein-G column (GE healthcare).

Example 9

Characterization of Humanized Anti-CTLA4 Antibodies in Binding Activity and Specificity, and Ligand Blockage Activity After generation and purification of humanized 6F3-hIgG1 and 10B10-hIgG1 antibodies, the binding and specificity of the antibodies were determined using ELISA-based binding and CTLA4/CD80 blockage analyses, as well as FACS-based binding and CTLA4/CD80 blockage analyses. The methods used were similar to those described above in EXAMPLE 4.

Figure 5:
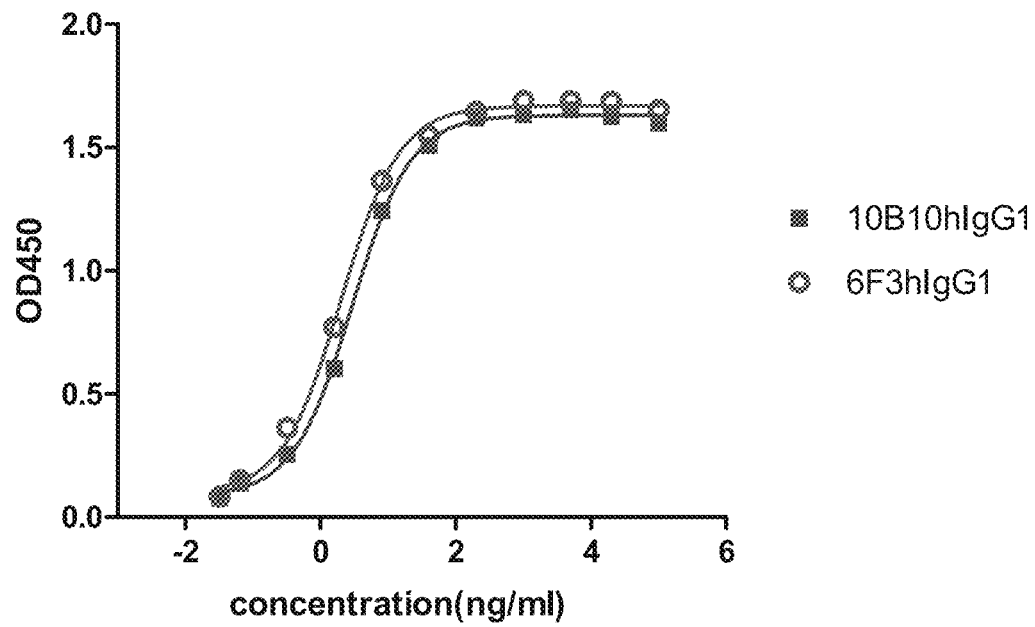
FIG. 5 is the graph showing the binding EC50 of humanized antibody 6F3 and 10B10 as measured by ELISA. The top panel of the figure shows the absorbance over a range of concentrations of humanized antibodies, and the bottom panel of the figure shows the calculated EC50 of each of the test antibodies.

FIG. 5 (top panel) exhibited the CTLA4 binding curve of humanized 6F3 and 10B10 antibodies, respectively. The bottom panel of FIG. 5 show the EC50 for each of the antibodies tested, calculated from the ELISA binding data, and demonstrate that the humanized 6F3 and 10B10 antibodies can bind with CTLA4. In contrast, the hIgG1 isotype control antibody did not exhibit any CTLA4 binding.

Figure 6:
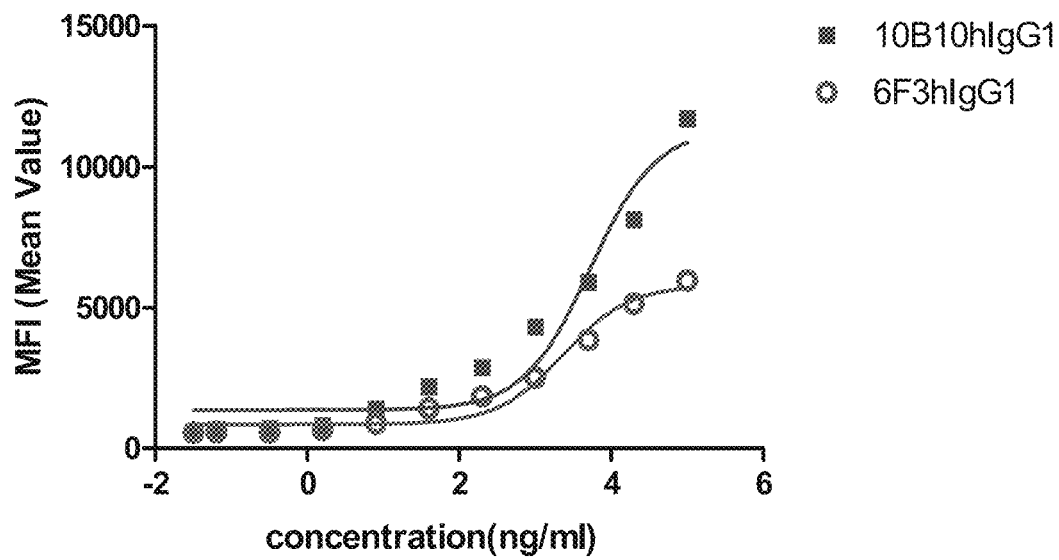
FIG. 6 shows the binding EC50 of humanized antibody 6F3 and 10B10 as measured by FACS. The top panel of the figure shows the mean fluorescence intensity (MFI) over a range of concentrations of humanized antibodies, and the bottom panel of the figure shows the calculated EC50 of each of the test antibodies.

Similarly, in the FACS-based binding assays, both humanized 6F3 and 10B10 antibody (FIG. 6, top panel) demonstrated strong binding with CTLA4. The EC50 calculated from the FACS binding data for humanized 6F3 and 10B10 antibodies is shown in the bottom panel of FIG. 6, respectively.

Figure 7:
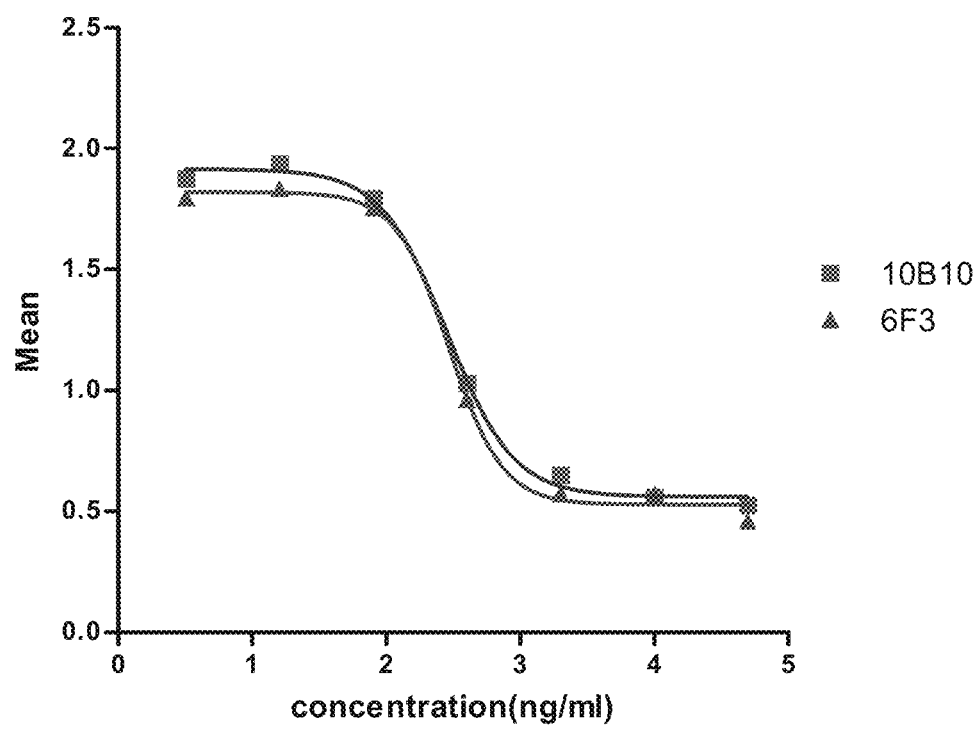
FIG. 7 shows blockage of CTLA4 ligand CD80 binding to CTLA4 by humanized anti-CTLA4 antibody 6F3 and 10B10 as measured by ELISA. The top panel of figure shows the absorbance over a range of antibody concentrations. The blockage IC50 for the anti-CTLA4 antibodies is shown in the bottom panel of FIG. 7.

FIG. 7 (top panel) shows the results of the ELISA-based ligand blocking assays for humanized 6F3 and humanized 10B10 antibodies, respectively. Quantification of the IC50 for each of the humanized antibody is shown in the bottom panels of FIG. 7.

Figure 8:
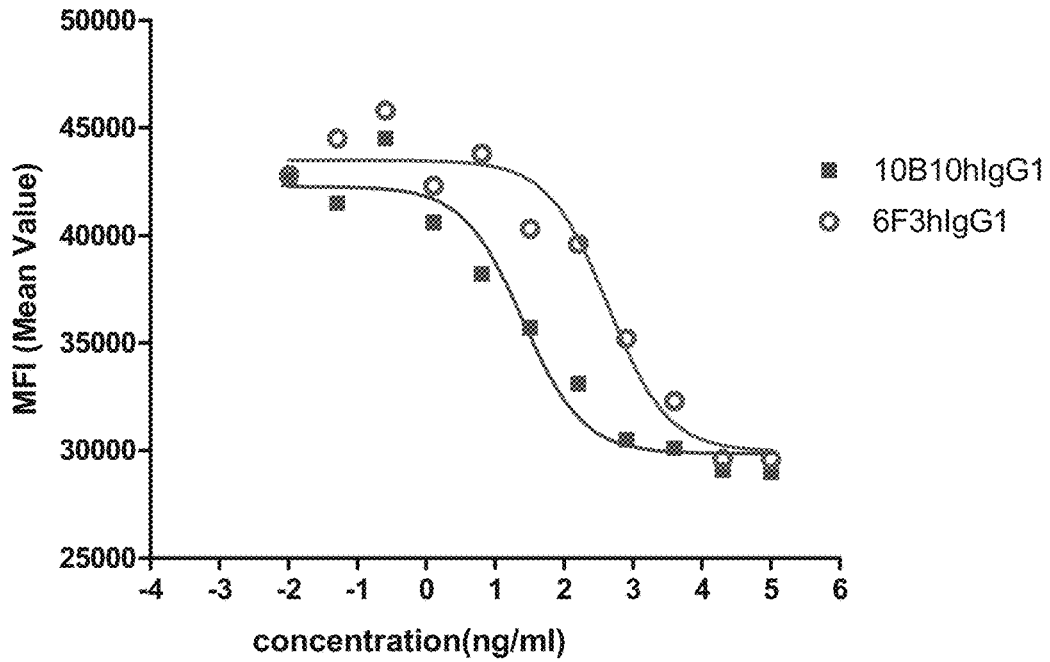
FIG. 8 shows blockage of CTLA4 ligand CD80 binding to CTLA4 by humanized anti-CTLA4 antibody 6F3 and 10B10 as measured by FACS. The top panel of the figure shows the MFI over a range of antibody concentrations. The blockage IC50 for the anti-CTLA4 antibodies is shown in the bottom panel of FIG. 8.

FIG. 8 shows that both humanized 6F3 and humanized 10B10 antibody blocked CTLA4 binding with CD80, as measured by FACS-based ligand blockage assay. The bottom panel of FIG. 8 provides the IC50 for each of the humanized antibodies.

TABLE 11

ELISA based binding EC50 of humanized anti-CTLA4 antibodies

| ng/ml | 6F3 | 10B10 |
| --- | --- | --- |
| EC50 | 2.012 | 2.932 |

TABLE 12

ELISA based blockage IC50 of humanized anti-CTLA4 antibodies

| ng/ml | 6F3 | 10B10 |
| --- | --- | --- |
| IC50 | 295.1 | 284.9 |

TABLE 13

FACS based binding EC50 of humanized anti-CTLA4 antibodies

| ng/ml | 6F3 | 10B10 |
| --- | --- | --- |
| EC50 | 2335 | 5279 |

TABLE 14

FACS based blockage IC50 of humanized anti-CTLA4 antibodies

| ng/ml | 6F3 | 10B10 |
| --- | --- | --- |
| IC50 | 435.1 | 25.27 |

Example 10

Biacore Kinetic Analysis of the Humanized 6F3 and 10B10 Antibodies

The binding kinetics between CTLA4 and humanized CTLA4 antibodies were measured by Biacore3000 as described in Example 5. The dissociation constant, KD, was calculated from the determined rate constants by the relation KD=kd/ka. As shown in Table 15, the humanized anti-CTLA4 antibodies 6F3 and 10B10 bound human CTLA4 with similar affinity to their murine counterparts.

TABLE 15

Binding kinetics of humanized anti-CTLA4 antibodies with CTLA4.

| | ka (1/Ms) | kd (1/s) | Kd (M) | Chi2 |
| --- | --- | --- | --- | --- |
| 6F3 | 2.95E+05 | 1.30E−04 | 4.41E−10 | 0.27 |
| 10B10 | 4.14E+05 | 1.13E−04 | 2.73E−10 | 0.79 |

Example 11

Effect of Humanized Anti-CTLA4 Antibodies on Cytokine Production by PBMC

Figure 11:
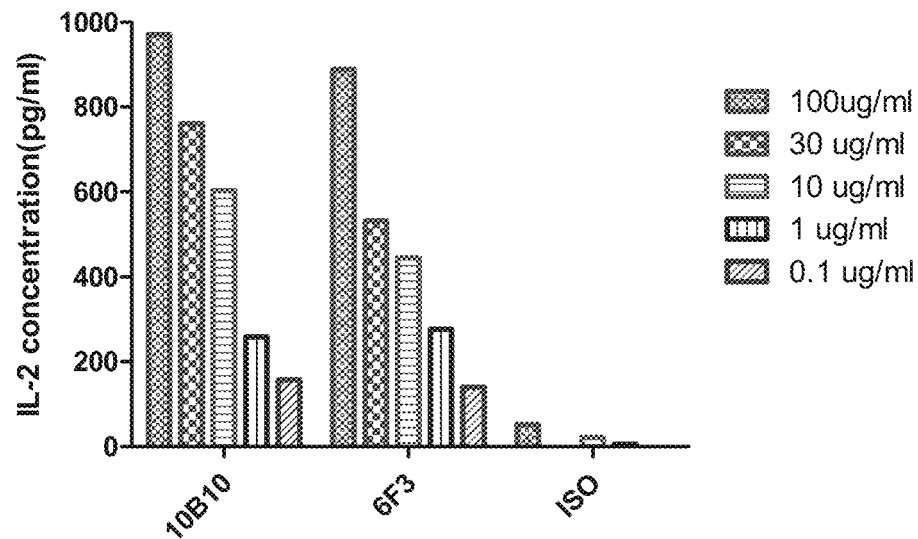
FIG. 11 is a graph showing IL-2 (pg/mL) production by PBMC in response to different concentrations of humanized anti-CTLA4 antibodies. The humanized anti-CTLA4 antibodies tested were, from left to right, 10B10, 6F3, hIgG1 isotype control. As shown on the x-axis, each antibody was tested at 30 µg/mL, 10 µg/mL, 1 µg/mL.
Figure 12:
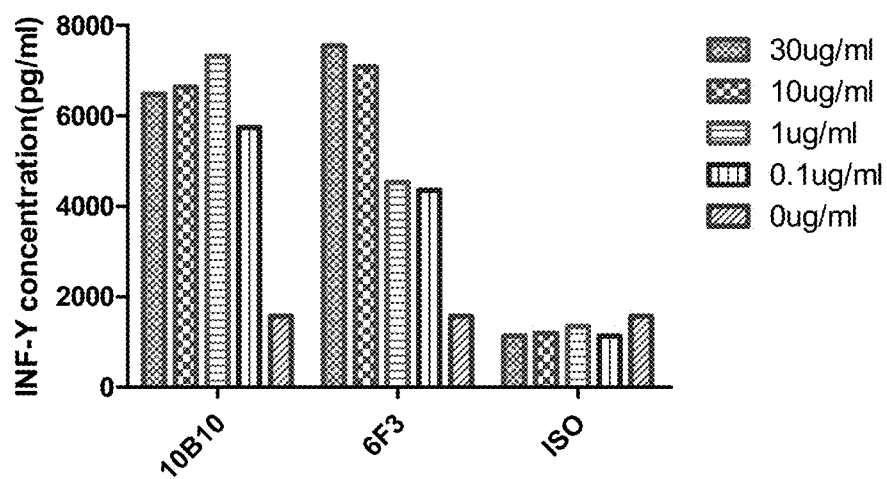
FIG. 12 is a graph showing IFN-γ (pg/mL) production by PBMC in response to different concentrations of humanized anti-CTLA4 antibodies. The humanized anti-CTLA4 antibodies tested were, from left to right, 10B10, 6F3, mIgG1 isotype control. As shown on the x-axis, each antibody was tested at 30 µg/mL, 10 µg/mL, 1 µg/mL.

The activity of humanized CTLA4 antibody was evaluated by its effect on blocking the CTLA4 signaling pathway in lymphocyte effector cells, as described in Example 6. The results of the study are provided in FIG. 11 (IL-2 secretion) and FIG. 12 (IFN-γ secretion), demonstrating that the anti-CTLA4 monoclonal antibody 6F3 and 10B10 can promote IFN-γ and IL-2 secretion. In contrast, cultures containing the isotype control antibody did not show an increase in IFN-γ or IL-2 secretion.

Example 12

Effect of Humanized CTLA4 Antibody on Tumor Growth Inhibition

The in vivo antitumor activity of humanized 10B10 antibody was evaluated using CTLA4 HuGEMM, a type of genetically engineered mouse model (GEMM) with chimeric human/mouse CTLA4 gene containing humanized exon 2 and exon 3 in C57BL/6 mice. Each mouse was inoculated subcutaneously at the right hind flank with MC38 mouse colon adenocarcinoma cells ($1 \times 10^6$) for tumor development. When average tumor size reached about 75 mm$^3$, mice were randomly grouped based on their tumor sizes with antibody treatment started on the same day. The isotype control and test antibodies were freshly formulated with PBS to 1 mg/mL and dosed to the mice via intraperitoneal injection (i.p.) at 10 mg/kg, twice weekly (BIW) for 3 weeks. Tumor sizes and body weights were measured BIW, and tumor growth inhibition (TGI) calculated as (1−(TVday21−TVday0 in treatment group/TVday21−TVday0 in control group)×100%).

Figure 13:
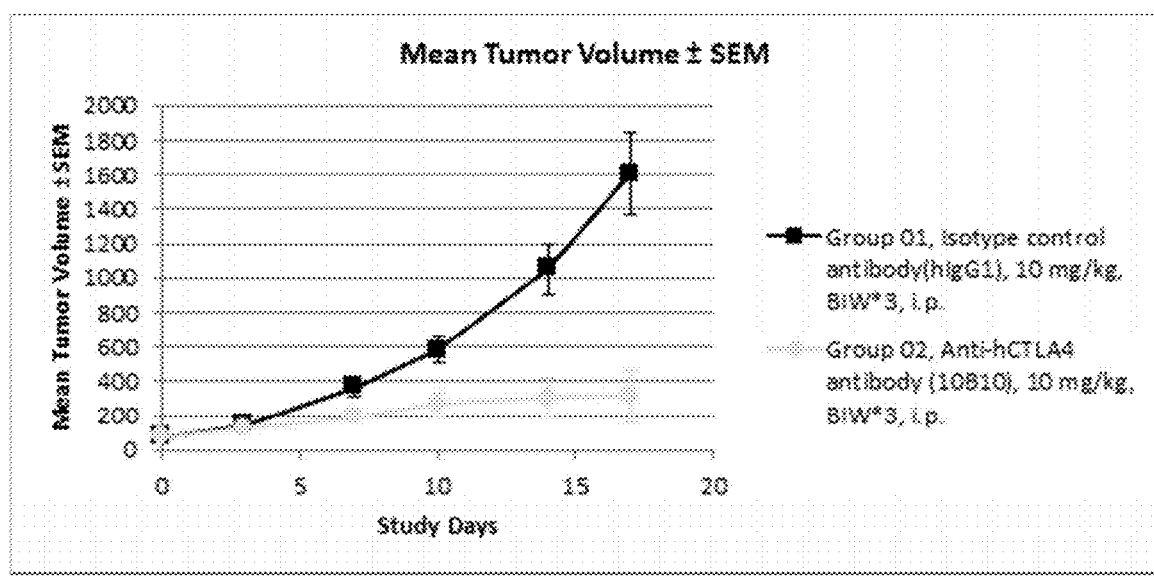
FIG. 13 is a graph showing the inhibitory effect of humanized CTLA4 antibody on tumor growth in HuGEMM model

As shown in FIG. 13, humanized anti-CTLA4 antibody 10B10 in groups 2 produced significant antitumor activity (p≤0.001) with their TGI 84.85% on day 21.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. An isolated antibody or antigen-binding fragment thereof, comprising a heavy chain variable region comprising complementary determining region (CDR)1 of SEQ ID NO: 3, CDR2 of SEQ ID NO: 5, and CDR3 of SEQ ID NO: 7, and a light chain variable region comprising CDR1 of SEQ ID NO: 11, CDR2 of SEQ ID NO: 13, and CDR3 of SEQ ID NO: 15; or
 a heavy chain variable region comprising CDR1 of SEQ ID NO: 19, CDR2 of SEQ ID NO: 21, and CDR3 of SEQ ID NO: 23, and a light chain variable region comprising CDR1 of SEQ ID NO: 27, CDR2 of SEQ ID NO: 29, and CDR3 of SEQ ID NO: 31.

2. The antibody or antigen-binding fragment thereof of claim 1, comprising:
 a) a heavy chain variable region comprising SEQ ID NO: 1 and a light chain variable region comprising SEQ ID NO: 9; or
 b) a heavy chain variable region comprising SEQ ID NO: 17 and a light chain variable region comprising SEQ ID NO: 25; or
 c) a heavy chain variable region comprising SEQ ID NO: 33 and a light chain variable region comprising SEQ ID NO: 35; or
 d) a heavy chain variable region comprising SEQ ID NO: 37 and a light chain variable region comprising SEQ ID NO: 39.

3. The antibody or antigen-binding fragment thereof of claim 1, which is a humanized monoclonal antibody.

4. The antibody or antigen-binding fragment thereof of claim 1, which is a diabody, a scFv, an scFv dimer, a BsFv, a dsFv, a (dsFv)2, a dsFv-dsFv', an Fv fragment, a Fab, a Fab', a F(ab')2, or a ds diabody.

5. The antibody or antigen-binding fragment thereof of claim 1, further comprising a conjugate.

6. An isolated polynucleotide encoding the antibody or an antigen-binding fragment thereof of claim 1.

7. A vector comprising the isolated polynucleotide of claim 6.

8. A culture comprising a host cell comprising the vector of claim 7.

9. A method of expressing the antibody or antigen-binding fragment thereof of claim 1, comprising culturing a culture comprising a host cell comprising a vector comprising an isolated polynucleotide encoding the antibody or an antigen-binding fragment thereof under the condition at which the polynucleotide is expressed.

10. A kit comprising the antibody or antigen-binding fragment thereof of claim 1.

11. A method of treating a cancer in an individual, comprising: administering a therapeutically effective amount of antibody or antigen-binding fragment thereof of claim 1 to the individual.

12. The method of claim 11, wherein the individual has been identified as having the cancer likely to respond to a CTLA4 inhibitor.

13. A pharmaceutical composition comprising the antibody or antigen-binding fragment thereof of claim 1 and one or more pharmaceutically acceptable carriers.

* * * * *

SEQUENCE LISTING

<160> NUMBER OF SEQ ID NOS: 54

<210> SEQ ID NO 1
<211> LENGTH: 123
<212> TYPE: PRT
<213> ORGANISM: Mus musculus

<400> SEQUENCE: 1

Gln Val Lys Leu Gln Glu Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Met Lys Gln Thr Pro Val His Gly Leu Glu Trp Ile
        35                  40                  45

Gly Val Ile Asp Pro Glu Thr Gly Gly Ile Thr Tyr Asn Gln Lys Phe
    50                  55                  60

Lys Gly Lys Ala Thr Leu Thr Ala Asp Lys Ser Ser Thr Ala Tyr
65                  70                  75                  80

Met Glu Phe Leu Ser Leu Thr Ser Glu Asp Ser Ala Val Tyr Tyr Cys
                85                  90                  95

Thr Arg Arg Gly Ala Arg Ala Thr Val Tyr Asn Tyr Val Met Asp Tyr
            100                 105                 110

Trp Gly Gln Gly Thr Ser Val Thr Val Ser Ser
        115                 120

<210> SEQ ID NO 2
<211> LENGTH: 369
<212> TYPE: DNA
<213> ORGANISM: Mus musculus

<400> SEQUENCE: 2
caggtcaagc tgcaggagtc tggggctgag ctggtgaggc ctggggcttc agtgacgctg      60
tcctgcaagg cttcgggcta cacatttact gactatgaaa tgcactggat gaagcagaca     120
cctgtgcatg gcctggaatg gattggagtt attgatcctg aaactggtgg tattacctac     180
aatcagaagt tcaagggcaa ggccacactg actgcagaca atcctccag cacagcctac      240 atggagttcc tcagcctgac atctgaggac tctgccgtct attactgtac aagacgggga     300
gctcgggcta ccgtatataa ctatgttatg gactattggg gtcaaggaac ctcagtcacc     360
gtctcctca                                                            369

<210> SEQ ID NO 3
<211> LENGTH: 5
<212> TYPE: PRT
<213> ORGANISM: Mus musculus

<400> SEQUENCE: 3

Asp Tyr Glu Met His
1               5

<210> SEQ ID NO 4
<211> LENGTH: 15

-continued

<210> SEQ ID NO 4
<211> LENGTH: 15
<212> TYPE: DNA
<213> ORGANISM: Mus musculus

<400> SEQUENCE: 4
gactatgaaa tgcac                                                      15

<210> SEQ ID NO 5
<211> LENGTH: 17
<212> TYPE: PRT
<213> ORGANISM: Mus musculus

<400> SEQUENCE: 5

Val Ile Asp Pro Glu Thr Gly Gly Ile Thr Tyr Asn Gln Lys Phe Lys
1               5                   10                  15

Gly

<210> SEQ ID NO 6
<211> LENGTH: 51
<212> TYPE: DNA
<213> ORGANISM: Mus musculus

<400> SEQUENCE: 6
gttattgatc ctgaaactgg tggtattacc tacaatcaga gttcaaggg c                51

<210> SEQ ID NO 7
<211> LENGTH: 14
<212> TYPE: PRT
<213> ORGANISM: Mus musculus

<400> SEQUENCE: 7

Arg Gly Ala Arg Ala Thr Val Tyr Asn Tyr Val Met Asp Tyr
1               5                   10

<210> SEQ ID NO 8
<211> LENGTH: 42
<212> TYPE: DNA
<213> ORGANISM: Mus musculus

<400> SEQUENCE: 8
cggggagctc gggctaccgt atataactat gttatggact at                        42

<210> SEQ ID NO 9
<211> LENGTH: 107
<212> TYPE: PRT
<213> ORGANISM: Mus musculus

<400> SEQUENCE: 9

Asp Ile Val Met Thr Gln Thr Thr Ala Ser Leu Ser Ala Ser Val Gly
1               5                   10                  15

Glu Thr Val Thr Ile Thr Cys Arg Ala Ser Glu Asn Ile His Asn Tyr
            20                  25                  30

Leu Ala Trp Tyr Gln Gln Lys Gln Gly Arg Ser Pro Gln Leu Leu Val
        35                  40                  45

Tyr Asn Ala Lys Thr Leu Gly Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys
            100                 105

<210> SEQ ID NO 10
<211> LENGTH: 321
<212> TYPE: DNA
<213> ORGANISM: Mus musculus

<400> SEQUENCE: 10

```
gacattgtga tgacccagac tacagcctcc ctatctgcat ctgtgggaga aactgtcacc    60
atcacatgtc gagcaagtga gaatattcac aattatttag catggtatca acagaaacag   120
ggaagatctc ctcagctcct ggtctataat gcaaaaacct taggagatgg tgtgccatca   180
aggttcagtg gcagtggatc aggaacacaa tattctctca agatcaacag cctgcagcct   240
gaagattttg ggagttatta ctgtcaacat ttttggagta ctccgtggac gttcggtgga   300
ggcaccaagc tggaaatcaa a                                             321
```

<210> SEQ ID NO 11
<211> LENGTH: 11
<212> TYPE: PRT
<213> ORGANISM: Mus musculus

<400> SEQUENCE: 11

Arg Ala Ser Glu Asn Ile His Asn Tyr Leu Ala
1               5                   10

<210> SEQ ID NO 12
<211> LENGTH: 33
<212> TYPE: DNA
<213> ORGANISM: Mus musculus

<400> SEQUENCE: 12

```
cgagcaagtg agaatattca caattattta gca                                 33
```

<210> SEQ ID NO 13
<211> LENGTH: 7
<212> TYPE: PRT
<213> ORGANISM: Mus musculus

<400> SEQUENCE: 13

Asn Ala Lys Thr Leu Gly Asp
1               5

<210> SEQ ID NO 14
<211> LENGTH: 21
<212> TYPE: DNA
<213> ORGANISM: Mus musculus

<400> SEQUENCE: 14

```
aatgcaaaaa ccttaggaga t                                              21
```

<210> SEQ ID NO 15
<211> LENGTH: 9
<212> TYPE: PRT
<213> ORGANISM: Mus musculus

<400> SEQUENCE: 15

Gln His Phe Trp Ser Thr Pro Trp Thr
1               5

<210> SEQ ID NO 16
<211> LENGTH: 27
<212> TYPE: DNA
<213> ORGANISM: Mus musculus

<400> SEQUENCE: 16
caacattttt ggagtactcc gtggacg                                           27

<210> SEQ ID NO 17
<211> LENGTH: 119
<212> TYPE: PRT
<213> ORGANISM: Mus musculus

<400> SEQUENCE: 17

Asp Val Gln Leu Gln Glu Ser Gly Pro Gly Leu Val Thr Pro Ser Gln
1               5                   10                  15

Ser Leu Ser Leu Thr Cys Ser Val Thr Gly Tyr Ser Ile Thr Ser Gly
            20                  25                  30

Tyr Ser Trp Asn Trp Ile Arg Gln Phe Pro Gly Asn Lys Leu Glu Trp
        35                  40                  45

Met Gly Tyr Ile Arg Phe Asp Gly Asn Asn Asn Tyr Asn Pro Phe Leu
    50                  55                  60

Lys Asn Arg Ile Ser Ile Thr Arg Asp Thr Ser Glu Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Asn Tyr Gly Thr Trp Gly Ala Met Asp Phe Trp Gly Gln Gly
            100                 105                 110

Thr Ser Val Thr Val Ser Ser
        115

<210> SEQ ID NO 18
<211> LENGTH: 357
<212> TYPE: DNA
<213> ORGANISM: Mus musculus

<400> SEQUENCE: 18
gatgtacagc ttcaggagtc aggacctggc ctcgtgacac cttctcagtc tctgtctctc    60
acctgctctg tcactggcta ctccatcacc agtggttatt cctggaactg gatccggcag   120
tttccaggaa acaaactgga atggatgggc tacataaggt tcgacggtaa caataactac   180
aacccatttc tcaaaaatcg aatctccatc actcgtgaca catctgagaa ccagtttttc   240
ctgaagttga attctgtgac tactgaggac acagctacat attactgtgc aagaaactat   300
ggtacctggg gggctatgga cttctggggt caaggaacct cagtcaccgt ctcctca      357

<210> SEQ ID NO 19
<211> LENGTH: 6
<212> TYPE: PRT
<213> ORGANISM: Mus musculus

<400> SEQUENCE: 19

Ser Gly Tyr Ser Trp Asn
1               5

<210> SEQ ID NO 20
<211> LENGTH: 18
<212> TYPE: DNA
<213> ORGANISM: Mus musculus

<400> SEQUENCE: 20
agtggttatt cctggaac                                                    18

<210> SEQ ID NO 21
<211> LENGTH: 16
<212> TYPE: PRT
<213> ORGANISM: Mus musculus

<400> SEQUENCE: 21

Tyr Ile Arg Phe Asp Gly Asn Asn Tyr Asn Pro Phe Leu Lys Asn
1               5                   10                  15

<210> SEQ ID NO 22
<211> LENGTH: 48
<212> TYPE: DNA
<213> ORGANISM: Mus musculus

<400> SEQUENCE: 22
tacataaggt tcgacggtaa caataactac aacccatttc tcaaaaat        48

<210> SEQ ID NO 23
<211> LENGTH: 10
<212> TYPE: PRT
<213> ORGANISM: Mus musculus

<400> SEQUENCE: 23

Asn Tyr Gly Thr Trp Gly Ala Met Asp Phe
1               5                   10

<210> SEQ ID NO 24
<211> LENGTH: 30
<212> TYPE: DNA
<213> ORGANISM: Mus musculus

<400> SEQUENCE: 24
aactatggta cctgggggc tatggacttc                              30

<210> SEQ ID NO 25
<211> LENGTH: 106
<212> TYPE: PRT
<213> ORGANISM: Mus musculus

<400> SEQUENCE: 25

Asp Ile Val Leu Thr Gln Ser Pro Ser Ser Leu Ser Ala Ser Leu Gly
1               5                   10                  15

Gly Lys Val Thr Ile Thr Cys Lys Thr Ser Gln Asp Ile Asn Lys Tyr
                20                  25                  30

Met Ala Trp Tyr Gln His Lys Pro Gly Lys Gly Pro Arg Leu Leu Ile
            35                  40                  45

Tyr Tyr Thr Ser Ile Leu Gln Pro Gly Ile Pro Ser Arg Phe Ser Gly
        50                  55                  60

Ser Gly Ser Gly Thr Asp Tyr Ser Phe Ser Ile Asn Asn Leu Glu Pro
65                  70                  75                  80

Glu Asp Ile Ala Thr Tyr Tyr Cys Gln Gln Tyr Asp Asn Leu Asn Thr
                85                  90                  95

Phe Gly Gly Gly Thr Met Leu Glu Ile Lys
            100                 105

<210> SEQ ID NO 26
<211> LENGTH: 318
<212> TYPE: DNA
<213> ORGANISM: Mus musculus

<400> SEQUENCE: 26
gatattgtgc tgacacagtc tccatcctca ctgtctgcat ctctgggagg caaagtcacc    60

```
atcacttgca agacaagcca agacattaat aaatatatgg cttggtacca acacaagcct      120
ggaaaaggtc ctaggctgct catatattac acatctatat tacagccggg catcccatcc      180
aggttcagtg gaagtgggtc tgggacagat tattccttca gcatcaacaa cctggagcct      240
gaagatattg caacttatta ttgtcaacag tatgataatc tgaacacatt cggagggggg      300
accatgttgg aaataaag                                                    318
```

<210> SEQ ID NO 27
<211> LENGTH: 11
<212> TYPE: PRT
<213> ORGANISM: Mus musculus

<400> SEQUENCE: 27

Lys Thr Ser Gln Asp Ile Asn Lys Tyr Met Ala
1               5                   10

<210> SEQ ID NO 28
<211> LENGTH: 33
<212> TYPE: DNA
<213> ORGANISM: Mus musculus

<400> SEQUENCE: 28

```
aagacaagcc aagacattaa taaatatatg gct                                    33
```

<210> SEQ ID NO 29
<211> LENGTH: 7
<212> TYPE: PRT
<213> ORGANISM: Mus musculus

<400> SEQUENCE: 29

Tyr Thr Ser Ile Leu Gln Pro
1               5

<210> SEQ ID NO 30
<211> LENGTH: 21
<212> TYPE: DNA
<213> ORGANISM: Mus musculus

<400> SEQUENCE: 30

```
tacacatcta tattacagcc g                                                 21
```

<210> SEQ ID NO 31
<211> LENGTH: 8
<212> TYPE: PRT
<213> ORGANISM: Mus musculus

<400> SEQUENCE: 31

Gln Gln Tyr Asp Asn Leu Asn Thr
1               5

<210> SEQ ID NO 32
<211> LENGTH: 24
<212> TYPE: DNA
<213> ORGANISM: Mus musculus

<400> SEQUENCE: 32

```
caacagtatg ataatctgaa caca                                              24
```

<210> SEQ ID NO 33
<211> LENGTH: 123
<212> TYPE: PRT
<213> ORGANISM: Artificial Sequence

```
<220> FEATURE:
<223> OTHER INFORMATION: Synthetic

<400> SEQUENCE: 33

Gln Val Gln Leu Val Gln Ser Gly Ala Glu Val Lys Pro Gly Ser
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Ile
            35                  40                  45

Gly Val Ile Asp Pro Glu Thr Gly Gly Ile Thr Tyr Asn Gln Lys Phe
        50                  55                  60

Lys Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Arg Gly Ala Arg Ala Thr Val Tyr Asn Tyr Val Met Asp Tyr
            100                 105                 110

Trp Gly Gln Gly Thr Leu Val Thr Val Ser Ser
        115                 120

<210> SEQ ID NO 34
<211> LENGTH: 369
<212> TYPE: DNA
<213> ORGANISM: Artificial Sequence
<220> FEATURE:
<223> OTHER INFORMATION: Synthetic

<400> SEQUENCE: 34
caggtgcagc tggtgcagtc tggagcagag gtgaagaagc caggcagctc cgtgaaggtg     60
tcttgtaagg ccagcggcta caccttcaca gactatgaga tgcactgggt gcggcaggca    120
ccaggacagg gactggagtg gatcggcgtg atcgatcctg agaccggcgg catcacatac    180
aaccagaagt ttaagggcag ggccaccctg acagccgaca gagcacctc cacagcctat    240 atggagctgt ctagcctgag gtccgaggat accgccgtgt actattgcac acggagaggc    300
gccagagcca ccgtgtacaa ttatgtgatg gactactggg gccagggcac cctggtgaca    360
gtctcgagc                                                            369

<210> SEQ ID NO 35
<211> LENGTH: 107
<212> TYPE: PRT
<213> ORGANISM: Artificial Sequence
<220> FEATURE:
<223> OTHER INFORMATION: Synthetic

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile His Asn Tyr
                20                  25                  30

Leu Ala Trp Tyr Gln Gln Lys Pro Gly Lys Ala Pro Lys Leu Leu Val
            35                  40                  45

Tyr Asn Ala Lys Thr Leu Gly Asp Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Thr Pro Trp
```

Thr Phe Gly Gly Gly Thr Lys Val Glu Ile Lys
                    100                 105

<210> SEQ ID NO 36
<211> LENGTH: 321
<212> TYPE: DNA
<213> ORGANISM: Artificial Sequence
<220> FEATURE:
<223> OTHER INFORMATION: Synthetic

<400> SEQUENCE: 36

```
gacatccaga tgacacagtc ccctagctcc ctgtccgcct ctgtgggcga tagggtgacc    60
atcacatgta gagcctctga acatccacaa attacctggg cctggtatca gcagaagccc   120
ggcaaggccc ctaagctgct ggtgtacaac gcaaagaccc tgggcgacgg agtgccatct   180
cggttcagcg gatccggatc tggcacagac tataccctga caatctctag cctgcagcca   240
gaggattttg ccacctacta ttgccagcac ttctggagca cccccctgga catttggcggc   300
ggcaccaagg tggagatcaa g                                              321
```

<210> SEQ ID NO 37
<211> LENGTH: 119
<212> TYPE: PRT
<213> ORGANISM: Artificial Sequence
<220> FEATURE:
<223> OTHER INFORMATION: Synthetic

<400> SEQUENCE: 37

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Thr Ser Gly
            20                  25                  30

Tyr Ser Trp Asn Trp Ile Arg Gln Pro Pro Gly Lys Gly Leu Glu Trp
        35                  40                  45

Met Gly Tyr Ile Arg Phe Asp Gly Asn Asn Asn Tyr Asn Pro Phe Leu
    50                  55                  60

Lys Asn Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asn Tyr Gly Thr Trp Gly Ala Met Asp Phe Trp Gly Gln Gly
            100                 105                 110

Thr Leu Val Thr Val Ser Ser
        115

<210> SEQ ID NO 38
<211> LENGTH: 357
<212> TYPE: DNA
<213> ORGANISM: Artificial Sequence
<220> FEATURE:
<223> OTHER INFORMATION: Synthetic

<400> SEQUENCE: 38

```
caggtgcagc tgcaggagtc cggaccagga ctggtgaagc catctcagac cctgagcctg    60
acatgtgccg tgtccggcta ctctatcacc agcggctatt cctggaattg gatcaggcag   120
ccacctggca agggactgga gtggatgggc tacatccgct tcgatggcaa caataactat   180
aatccctttc tgaagaaccg gatcaccatc tccagagaca catctaagaa tcagttctcc   240
```

```
ctgaagctga gctccgtgac cgcagcagat acagccgtgt actattgcgc aaggaactac      300
ggaacatggg gagcaatgga cttttggggc cagggcaccc tggtgacagt ctcgagc         357
```

<210> SEQ ID NO 39
<211> LENGTH: 106
<212> TYPE: PRT
<213> ORGANISM: Artificial Sequence
<220> FEATURE:
<223> OTHER INFORMATION: Synthetic

<400> SEQUENCE: 39

```
Asp Ile Gln Leu Thr Gln Ser Pro Ser Leu Ser Ala Ser Val Gly
1               5                   10                  15

Asp Arg Val Thr Ile Thr Cys Lys Thr Ser Gln Asp Ile Asn Lys Tyr
            20                  25                  30

Met Ala Trp Tyr Gln Gln Lys Pro Gly Lys Ala Pro Lys Leu Leu Ile
        35                  40                  45

Tyr Tyr Thr Ser Ile Leu Gln Pro Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Asp Asn Leu Asn Thr
                85                  90                  95

Phe Gly Gly Gly Thr Lys Val Glu Ile Lys
            100                 105
```

<210> SEQ ID NO 40
<211> LENGTH: 318
<212> TYPE: DNA
<213> ORGANISM: Artificial Sequence
<220> FEATURE:
<223> OTHER INFORMATION: Synthetic

<400> SEQUENCE: 40

```
gacatccagc tgacccagtc ccctagctcc ctgtccgcct ctgtgggcga cagggtgacc       60
atcacctgta agacatctca ggatatcaac aagtacatgg cctggtatca gcagaagcca      120
ggcaaggccc ccaagctgct gatctactat acctctatcc tgcagcccgg cgtgcctagc      180
agattcagcg gctccggctc tggcaccgat tacacctttta caatctctag cctgcagccc     240
gaggacatcg ccacatacta ttgccagcag tatgataacc tgaatacctt tggcggcggc     300
acaaaggtgg agatcaag                                                    318
```

<210> SEQ ID NO 41
<211> LENGTH: 453
<212> TYPE: PRT
<213> ORGANISM: Artificial Sequence
<220> FEATURE:
<223> OTHER INFORMATION: Synthetic

<400> SEQUENCE: 41

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Val Ile Asp Pro Glu Thr Gly Gly Ile Thr Tyr Asn Gln Lys Phe
    50                  55                  60
```

Lys Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Thr Arg Arg Gly Ala Arg Ala Thr Val Tyr Asn Tyr Val Met Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 42
<211> LENGTH: 1359
<212> TYPE: DNA

<213> ORGANISM: Artificial Sequence
<220> FEATURE:
<223> OTHER INFORMATION: Synthetic

<400> SEQUENCE: 42

```
caggtgcagc tggtgcagtc tggagcagag gtgaagaagc caggcagctc cgtgaaggtg      60
tcttgtaagg ccagcggcta caccttcaca gactatgaga tgcactgggt gcggcaggca     120
ccaggacagg gactggagtg gatcggcgtg atcgatcctg agaccggcgg catcacatac     180
aaccagaagt ttaagggcag ggccaccctg acagccgaca gagcacctc cacagcctat      240
atggagctgt ctagcctgag gtccgaggat accgccgtgt actattgcac acggagaggc     300
gccagagcca ccgtgtacaa ttatgtgatg gactactggg gccagggcac cctggtgaca     360
gtctcgagcg cctccaccaa gggcccatcc gtgttccctc tggcaccctc agcaagagc      420
acaagcggag gcaccgccgc actgggctgc ctcgtgaagg actacttccc agaacccgtg     480
accgtcagct ggaatagcgg cgctctgacc agcggagtcc acactttccc cgcagtgctg     540
cagtccagcg gcctgtacag cctgagcagc gtggtcactg tgccaagcag cagcctgggc     600
actcagacct acatctgcaa cgtcaaccac aagcccagca cacaaaaggt ggacaagagg     660
gtcgagccca gtcctgcga taagacccac acctgccctc catgtcccgc ccccgagctg     720
ctgggaggac cagcgtcttc ctgtttccc cccaagccaa aggacaccct gatgatcagc     780
aggacccccg aagtgacctg cgtcgtggtg gacgtgagcc acgaagatcc cgaggtgaag     840
ttcaactggt acgtggacgg cgtggaagtg cacaacgcca agacaaaacc cagggaggag     900
cagtataaca gcacctacag ggtcgtgagc gtcctgaccg tgctgcacca agactggctg     960
aacggcaagg agtataagtg caaggtgagc aacaaggcac tgcccgcccc catcgagaag    1020
accatttcca aggccaaggg gcaacctagg gagccacagg tctacactct gcccccctagc   1080
agggacgagc tgaccaagaa ccaggtctcc ctgacttgcc tggtgaaggg gttttatccc    1140
agcgacatcg ccgtcgagtg ggagagcaat ggccagcccg aaaacaacta caagaccaca    1200
ccccctgtgc tggacagcga cggcagcttc tttctgtata gcaaactgac agtggataag    1260
agcagatggc agcagggcaa cgtgttctcc tgctccgtga tgcacgaggc cctgcacaat    1320
cactacaccc agaagtccct gagcctgagc cccggcaaa                           1359
```

<210> SEQ ID NO 43
<211> LENGTH: 214
<212> TYPE: PRT
<213> ORGANISM: Artificial Sequence
<220> FEATURE:
<223> OTHER INFORMATION: Synthetic

<400> SEQUENCE: 43

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Glu Asn Ile His Asn Tyr
             20                  25                  30

Leu Ala Trp Tyr Gln Gln Lys Pro Gly Lys Ala Pro Lys Leu Leu Val
         35                  40                  45

Tyr Asn Ala Lys Thr Leu Gly Asp Gly Val Pro Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Ser Thr Pro Trp
                 85                  90                  95
```

```
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 44
<211> LENGTH: 645
<212> TYPE: DNA
<213> ORGANISM: Artificial Sequence
<220> FEATURE:
<223> OTHER INFORMATION: Synthetic

<400> SEQUENCE: 44

```
gacatccaga tgacacagtc ccctagctcc ctgtccgcct ctgtgggcga tagggtgacc    60
atcacatgta gagcctctga aacatccac aattacctgg cctggtatca gcagaagccc    120
ggcaaggccc ctaagctgct ggtgtacaac gcaaagaccc tgggcgacgg agtgccatct   180
cggttcagcg gatccggatc tggcacagac tatacctga caatctctag cctgcagcca    240
gaggattttg ccacctacta ttgccagcac ttctggagca ccccctggac atttggcggc    300
ggcaccaagg tggagatcaa gcgtacggtg gccgcaccaa gcgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga aaacacaaa gtctacgcct gcgaagtcac ccatcagggc    600
ctgagctcgc ccgtcacaaa gagctttaac agaggcgagt gctga    645
```

<210> SEQ ID NO 45
<211> LENGTH: 449
<212> TYPE: PRT
<213> ORGANISM: Artificial Sequence
<220> FEATURE:
<223> OTHER INFORMATION: Synthetic

<400> SEQUENCE: 45

```
Gln Val Gln Leu Gln Glu Ser Gly Pro Gly Leu Val Lys Pro Ser Gln
1               5                   10                  15
Thr Leu Ser Leu Thr Cys Ala Val Ser Gly Tyr Ser Ile Thr Ser Gly
            20                  25                  30
Tyr Ser Trp Asn Trp Ile Arg Gln Pro Pro Gly Lys Gly Leu Glu Trp
        35                  40                  45
Met Gly Tyr Ile Arg Phe Asp Gly Asn Asn Asn Tyr Asn Pro Phe Leu
    50                  55                  60
```

```
Lys Asn Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
             85                  90                  95

Ala Arg Asn Tyr Gly Thr Trp Gly Ala Met Asp Phe Trp Gly Gln Gly
        100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 46
<211> LENGTH: 1347
<212> TYPE: DNA
<213> ORGANISM: Artificial Sequence
```

```
<220> FEATURE:
<223> OTHER INFORMATION: Synthetic

<400> SEQUENCE: 46
caggtgcagc tgcaggagtc cggaccagga ctggtgaagc catctcagac cctgagcctg      60
acatgtgccg tgtccggcta ctctatcacc agcggctatt cctggaattg gatcaggcag     120
ccacctggca agggactgga gtggatgggc tacatccgct cgatggcaa caataactat      180
aatcccttc tgaagaaccg gatcaccatc tccagagaca catctaagaa tcagttctcc      240
ctgaagctga gctccgtgac cgcagcagat acagccgtgt actattgcgc aaggaactac     300
ggaacatggg gagcaatgga cttttggggc cagggcaccc tggtgacagt ctcgagcgcc     360
tccaccaagg gcccatccgt gttccctctg caccctcca gcaagagcac aagcggaggc      420
accgccgcac tgggctgcct cgtgaaggac tacttcccag aacccgtgac cgtcagctgg     480
aatagcggcg ctctgaccag cggagtccac actttccccg cagtgctgca gtccagcggc     540
ctgtacagcc tgagcagcgt ggtcactgtg ccaagcagca gcctgggcac tcagacctac     600
atctgcaacg tcaaccacaa gcccagcaac acaaaggtgg acaagagggt cgagcccaag     660
tcctgcgata gacccacac ctgccctcca tgtcccgccc ccgagctgct gggaggaccc      720
agcgtcttcc tgtttccccc caagccaaag gacaccctga tgatcagcag gaccccgaa      780
gtgacctgcg tcgtggtgga cgtgagccac gaagatcccg aggtgaagtt caactggtac     840
gtggacggcg tggaagtgca acgccaag acaaaaccca gggaggagca gtataacagc       900
acctacaggg tcgtgagcgt cctgaccgtg ctgcaccaag actggctgaa cggcaaggag     960
tataagtgca aggtgagcaa caaggcactg cccgccccca tcgagaagac catttccaag    1020
gccaaggggc aacctaggga ccacaggtc tacactctgc cccctagcag ggacgagctg     1080
accaagaacc aggtctccct gacttgcctg gtgaagggt tttatcccag cgacatcgcc     1140
gtcgagtggg agagcaatgg ccagcccgaa acaactaca agaccacacc cctgtgctg      1200
gacagcgacg gcagcttctt tctgtatagc aaactgacag tggataagag cagatggcag    1260
cagggcaacg tgttctcctg ctccgtgatg cacgaggccc tgcacaatca ctacacccag    1320
aagtccctga gcctgagccc cggcaaa                                        1347

<210> SEQ ID NO 47
<211> LENGTH: 213
<212> TYPE: PRT
<213> ORGANISM: Artificial Sequence
<220> FEATURE:
<223> OTHER INFORMATION: Synthetic

<400> SEQUENCE: 47

Asp Ile Gln Leu Thr Gln Ser Pro Ser Ser Leu Ser Ala Ser Val Gly
1               5                   10                  15

Asp Arg Val Thr Ile Thr Cys Lys Thr Ser Gln Asp Ile Asn Lys Tyr
            20                  25                  30

Met Ala Trp Tyr Gln Gln Lys Pro Gly Lys Ala Pro Lys Leu Leu Ile
        35                  40                  45

Tyr Tyr Thr Ser Ile Leu Gln Pro Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Asp Asn Leu Asn Thr
                85                  90                  95
```

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 48
<211> LENGTH: 642
<212> TYPE: DNA
<213> ORGANISM: Artificial Sequence
<220> FEATURE:
<223> OTHER INFORMATION: Synthetic

<400> SEQUENCE: 48
gacatccagc tgacccagtc ccctagctcc ctgtccgcct ctgtgggcga cagggtgacc      60
atcacctgta agcatctca ggatatcaac aagtacatgg cctggtatca gcagaagcca     120
ggcaaggccc ccaagctgct gatctactat acctctatcc tgcagccgg cgtgcctagc     180 agattcagcg gctccggctc tggcaccgat tacaccttta caatctctag cctgcagccc     240
gaggacatcg ccacatacta ttgccagcag tatgataacc tgaatacctt tggcggcggc     300
acaaaggtgg agatcaagcg tacggtggcc gcaccaagcg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag ctttaacaga ggcgagtgct ga                       642

<210> SEQ ID NO 49
<211> LENGTH: 396
<212> TYPE: DNA
<213> ORGANISM: Artificial Sequence
<220> FEATURE:
<223> OTHER INFORMATION: Synthetic

<400> SEQUENCE: 49
aaagcaatgc acgtggccca gcctgctgtg gtactggcca gcagccgagg catcgccagc      60
tttgtgtgtg agtatgcatc tccaggcaaa gccactgagg tccgggtgac agtgcttcgg     120
caggctgaca gccaggtgac tgaagtctgt gcggcaacct acatgacggg gaatgagttg     180
accttcctag atgattccat ctgcacgggc acctccagtg gaaatcaagt gaacctcact     240
atccaaggac tgagggccat ggacacggga ctctacatct gcaaggtgga gctcatgtac     300
ccaccgccat actacctggg cataggcaac ggaacccaga tttatgtaat tgatccagaa     360
ccgtgcccag attctgacca tcatcaccac catcac                              396

<210> SEQ ID NO 50
<211> LENGTH: 132
<212> TYPE: PRT
<213> ORGANISM: Artificial Sequence
<220> FEATURE:
<223> OTHER INFORMATION: Synthetic

<400> SEQUENCE: 50

```
Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Thr Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp His His
        115                 120                 125

His His His His
    130
```

<210> SEQ ID NO 51
<211> LENGTH: 1368
<212> TYPE: DNA
<213> ORGANISM: Artificial Sequence
<220> FEATURE:
<223> OTHER INFORMATION: Synthetic

<400> SEQUENCE: 51

| | | | | | | |
|---|---|---|---|---|---|---|
| aaagcaatgc | acgtggccca | gcctgctgtg | gtactggcca | gcagccgagg | catcgccagc | 60 |
| tttgtgtgtg | agtatgcatc | tccaggcaaa | gccactgagg | tccgggtgac | agtgcttcgg | 120 |
| caggctgaca | gccaggtgac | tgaagtctgt | gcggcaacct | acatgacggg | gaatgagttg | 180 |
| accttcctag | atgattccat | ctgcacgggc | acctccagtg | gaaatcaagt | gaacctcact | 240 |
| atccaaggac | tgagggccat | ggacacggga | ctctacatct | gcaaggtgga | gctcatgtac | 300 |
| ccaccgccat | actacctggg | cataggcaac | ggaacccaga | tttatgtaat | tgatccagaa | 360 |
| ccgtgcccag | attctgacgc | caaaaccaca | gccccctccg | tgtatcctct | ggctcccgtc | 420 |
| tgcggagaca | caaccggcag | ctccgtcaca | ctgggctgtc | tcgtcaaggg | ctacttcccc | 480 |
| gagcctgtca | cactgacctg | gaactccggc | tccctgtcct | ccggagtgca | taccttcccc | 540 |
| gccgtgctcc | aatccgatct | gtacacactc | tccagcagcg | tcaccgtgac | ctccagcacc | 600 |
| tggcctagcc | agagcatcac | ctgcaatgtg | gcccaccctg | ccagcagcac | caaggtggac | 660 |
| aagaagatcg | agcctagggg | ccccaccatt | aaacccctgcc | ccccttgcaa | atgccctgct | 720 |
| cccaacctcc | tcggcggacc | ttccgtgttc | atttttcccc | ccaagatcaa | ggacgtgctc | 780 |
| atgatctccc | tgagccctat | cgtcacctgt | gtggtcgtgg | atgtgtccga | agatgatccc | 840 |
| gacgtgcaga | tctcctggtt | cgtcaacaat | gtggaggtgc | acacagccca | gacccagacc | 900 |
| cacagggagg | attataactc | caccctgagg | gtcgtcagcg | ctctccccat | ccagcaccag | 960 |

```
gactggatga gcggcaagga gttcaaatgc aaggtcaata ataaggacct gcccgccccc    1020
atcgagagga ccattagcaa acccaagggc agcgtcaggg ctccccaagt gtacgtgctg    1080
cctccccctg aggaggagat gaccaaaaag caggtcacac tcacctgcat ggtcaccgac    1140
ttcatgcccg aagatatcta cgtcgagtgg accaataacg aaagacagag gctcaactac    1200
aagaataccg agcctgtcct ggacagcgac ggcagctact tcatgtacag caagctgagg    1260
gtcgagaaga aaactgggt ggagaggaac agctacagct gttccgtggt ccacgagggc    1320
ctgcataacc accacaccac caaatccttc tccagaaccc ccggcaag                 1368
```

<210> SEQ ID NO 52
<211> LENGTH: 456
<212> TYPE: PRT
<213> ORGANISM: Artificial Sequence
<220> FEATURE:
<223> OTHER INFORMATION: Synthetic

<400> SEQUENCE: 52

```
Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Thr Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp Ala Lys
        115                 120                 125

Thr Thr Ala Pro Ser Val Tyr Pro Leu Ala Pro Val Cys Gly Asp Thr
    130                 135                 140

Thr Gly Ser Ser Val Thr Leu Gly Cys Leu Val Lys Gly Tyr Phe Pro
145                 150                 155                 160

Glu Pro Val Thr Leu Thr Trp Asn Ser Gly Ser Leu Ser Ser Gly Val
                165                 170                 175

His Thr Phe Pro Ala Val Leu Gln Ser Asp Leu Tyr Thr Leu Ser Ser
            180                 185                 190

Ser Val Thr Val Thr Ser Ser Thr Trp Pro Ser Gln Ser Ile Thr Cys
        195                 200                 205

Asn Val Ala His Pro Ala Ser Ser Thr Lys Val Asp Lys Lys Ile Glu
    210                 215                 220

Pro Arg Gly Pro Thr Ile Lys Pro Cys Pro Pro Cys Lys Cys Pro Ala
225                 230                 235                 240

Pro Asn Leu Leu Gly Gly Pro Ser Val Phe Ile Phe Pro Pro Lys Ile
                245                 250                 255

Lys Asp Val Leu Met Ile Ser Leu Ser Pro Ile Val Thr Cys Val Val
            260                 265                 270

Val Asp Val Ser Glu Asp Asp Pro Asp Val Gln Ile Ser Trp Phe Val
        275                 280                 285
```

Asn Asn Val Glu Val His Thr Ala Gln Thr Gln Thr His Arg Glu Asp
    290                 295                 300

Tyr Asn Ser Thr Leu Arg Val Val Ser Ala Leu Pro Ile Gln His Gln
305                 310                 315                 320

Asp Trp Met Ser Gly Lys Glu Phe Lys Cys Lys Val Asn Asn Lys Asp
                325                 330                 335

Leu Pro Ala Pro Ile Glu Arg Thr Ile Ser Lys Pro Lys Gly Ser Val
            340                 345                 350

Arg Ala Pro Gln Val Tyr Val Leu Pro Pro Glu Glu Met Thr
        355                 360                 365

Lys Lys Gln Val Thr Leu Thr Cys Met Val Thr Asp Phe Met Pro Glu
370                 375                 380

Asp Ile Tyr Val Glu Trp Thr Asn Asn Gly Lys Thr Glu Leu Asn Tyr
385                 390                 395                 400

Lys Asn Thr Glu Pro Val Leu Asp Ser Asp Gly Ser Tyr Phe Met Tyr
                405                 410                 415

Ser Lys Leu Arg Val Glu Lys Lys Asn Trp Val Glu Arg Asn Ser Tyr
            420                 425                 430

Ser Cys Ser Val Val His Glu Gly Leu His Asn His His Thr Thr Lys
        435                 440                 445

Ser Phe Ser Arg Thr Pro Gly Lys
    450                 455

<210> SEQ ID NO 53
<211> LENGTH: 1089
<212> TYPE: DNA
<213> ORGANISM: Artificial Sequence
<220> FEATURE:
<223> OTHER INFORMATION: Synthetic

<400> SEQUENCE: 53
aaagcaatgc acgtggccca gcctgctgtg gtactggcca gcagccgagg catcgccagc      60
tttgtgtgtg agtatgcatc tccaggcaaa gccactgagg tccgggtgac agtgcttcgg     120
caggctgaca gccaggtgac tgaagtctgt gcggcaacct acatgacggg gaatgagttg     180
accttcctag atgattccat ctgcacgggc acctccagtg gaaatcaagt gaacctcact     240
atccaaggac tgagggccat ggacacggga ctctacatct gcaaggtgga gctcatgtac     300
ccaccgccat actacctggg cataggcaac ggaacccaga tttatgtaat tgatccagaa     360
ccgtgcccag attctgacgg taccagatct agagagccca atcttctga caaaactcac     420 acatgcccac cgtgcccagc acctgaattc gagggtgcac cgtcagtctt cctcttcccc     480
ccaaaaccca aggacaccct catgatctcc cggactcctg aggtcacatg cgtggtggtg     540
gacgtaagcc acgaagaccc tgaggtcaag ttcaactggt acgtggacgg cgtggaggtg     600
cataatgcca agacaaagcc gcgggaggag cagtacaaca gcacgtaccg tgtggtcagc     660
gtcctcaccg tcctgcacca ggactggctg aatggcaagg agtacaagtg caaggtctcc     720
aacaaagccc tcccaacccc catcgagaaa accatctcca agccaaagg gcagccccga     780 gaaccacagg tgtacaccct gcccccatcc cgggatgagc tgaccaagaa ccaggtcagc     840
ctgacctgcc tggtcaaagg cttctatcca agcgacatcg ccgtggagtg ggagagcaat     900
gggcagccgg agaacaacta caagaccacg cctcccgtgc tggactccga cggctccttc     960
ttcctctaca gcaagctcac cgtggacaag agcaggtggc agcaggggaa cgtcttctca    1020
tgctccgtga tgcatgaggc tctgcacaac cactacacgc agaagagcct ctccctgtct    1080

```
ccgggtaaa                                                        1089
```

<210> SEQ ID NO 54
<211> LENGTH: 363
<212> TYPE: PRT
<213> ORGANISM: Artificial Sequence
<220> FEATURE:
<223> OTHER INFORMATION: Synthetic

<400> SEQUENCE: 54

```
Lys Ala Met His Val Ala Gln Pro Ala Val Leu Ala Ser Ser Arg
1               5                  10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Thr Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp Gly Thr
        115                 120                 125

Arg Ser Arg Glu Pro Lys Ser Ser Asp Lys Thr His Thr Cys Pro Pro
    130                 135                 140

Cys Pro Ala Pro Glu Phe Glu Gly Ala Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser His Glu Asp Pro Glu Val Lys Phe Asn
            180                 185                 190

Trp Tyr Val Asp Gly Val Glu Val His Asn Ala Lys Thr Lys Pro Arg
        195                 200                 205

Glu Glu Gln Tyr Asn Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Ala Leu Pro Thr Pro Ile Glu Lys Thr Ile Ser Lys Ala Lys
                245                 250                 255

Gly Gln Pro Arg Glu Pro Gln Val Tyr Thr Leu Pro Pro Ser Arg Asp
            260                 265                 270

Glu Leu Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
    290                 295                 300

Asn Asn Tyr Lys Thr Thr Pro Pro Val Leu Asp Ser Asp Gly Ser Phe
305                 310                 315                 320
```

-continued

```
Phe Leu Tyr Ser Lys Leu Thr Val Asp Lys Ser Arg Trp Gln Gln Gly
            325                 330                 335

Asn Val Phe Ser Cys Ser Val Met His Glu Ala Leu Asn His Tyr
            340                 345                 350

Thr Gln Lys Ser Leu Ser Leu Ser Pro Gly Lys
        355                 360
```